(12) United States Patent
Belliard et al.

(10) Patent No.: US 8,128,635 B2
(45) Date of Patent: Mar. 6, 2012

(54) BONE FIXATION TENSIONING TOOL AND METHOD

(75) Inventors: Karl Pierre Belliard, La Membrolle (FR); Gilles Larroque-Lahitette, Lagor (FR); Marion Jeanne Sophie Delclaud, Pau (FR); Jean-Luc Albert Paul Jouve, Marseille cedex (FR)

(73) Assignee: Zimmer Spine S.A.S., Bourdeaux (FR)

( * ) Notice: Subject to any disclaimer, the term of this patent is extended or adjusted under 35 U.S.C. 154(b) by 846 days.

(21) Appl. No.: 11/877,160

(22) Filed: Oct. 23, 2007

(65) Prior Publication Data

US 2009/0105715 A1    Apr. 23, 2009

(51) Int. Cl.
*A61B 17/70* (2006.01)
(52) U.S. Cl. ........................................ 606/103
(58) Field of Classification Search ............... 606/86 A, 606/86 R, 103
See application file for complete search history.

(56) References Cited

U.S. PATENT DOCUMENTS

| | | | |
|---|---|---|---|
| 902,040 A | 10/1908 | Wychoff | |
| 1,346,940 A | 7/1920 | Collins | |
| 2,049,361 A | 7/1936 | Ericsson | |
| 5,030,220 A | 7/1991 | Howland | |
| 5,304,178 A | 4/1994 | Stahurski | |
| 5,356,412 A | 10/1994 | Golds et al. | |
| 5,413,576 A | 5/1995 | Rivard | |
| 5,449,361 A * | 9/1995 | Preissman | 606/103 |
| 5,609,634 A | 3/1997 | Voydeville | |
| 5,667,508 A | 9/1997 | Errico | |
| 5,669,917 A | 9/1997 | Sauer et al. | |
| 5,702,399 A | 12/1997 | Kilpeta et al. | |
| 5,720,751 A * | 2/1998 | Jackson | 606/86 R |
| 5,935,133 A | 8/1999 | Wagner et al. | |
| 5,938,663 A | 8/1999 | Petreto | |
| 5,964,769 A | 10/1999 | Wagner et al. | |
| 6,053,921 A | 4/2000 | Wagner et al. | |
| 6,086,590 A | 7/2000 | Margulies et al. | |
| 6,099,527 A | 8/2000 | Hochschuler et al. | |
| 6,146,386 A | 11/2000 | Blackman et al. | |
| 6,179,838 B1 | 1/2001 | Fiz | |

(Continued)

FOREIGN PATENT DOCUMENTS

DE    19716 504    12/1998

(Continued)

OTHER PUBLICATIONS

European Search Report for EP 08305124.3, dated Oct. 10, 2008, 3 pages.

(Continued)

*Primary Examiner* — Eduardo C Robert
*Assistant Examiner* — Summer Kostelnik
(74) *Attorney, Agent, or Firm* — Seager Tufte & Wickhem LLC

(57) ABSTRACT

A tensioning tool and method for tensioning a conformable ligature of a bone fixing system are disclosed. The ends of a conformable ligature can be passed around bones, bone grafts, tendons, plates, rods, fasteners, or other anatomical or implanted structures, and the like to form a loop. Another portion of the conformable ligature can be coupled to a tensioning tool. The tensioning tool can include a first portion and a second portion in threaded engagement with each other. Rotation of one portion relative to the other can cause tensioning of the conformable ligature through translation of a tensioning member.

18 Claims, 21 Drawing Sheets

U.S. PATENT DOCUMENTS

| | | | |
|---|---|---|---|
| 6,228,096 B1 | 5/2001 | Marchand | |
| 6,241,740 B1 | 6/2001 | Davis et al. | |
| 6,277,120 B1 | 8/2001 | Lawson | |
| 6,309,390 B1 | 10/2001 | Le Couedic et al. | |
| 6,352,557 B1 | 3/2002 | Ferree | |
| 6,391,030 B1 | 5/2002 | Wagner et al. | |
| 6,419,702 B1 | 7/2002 | Ferree | |
| 6,447,518 B1 | 9/2002 | Krause et al. | |
| 6,478,798 B1 | 11/2002 | Howland | |
| 6,514,255 B1 | 2/2003 | Ferree | |
| 6,547,770 B2 | 4/2003 | Carlsson et al. | |
| 6,547,790 B2 | 4/2003 | Harkey, III et al. | |
| 6,569,164 B1 | 5/2003 | Assaker et al. | |
| 6,569,171 B2 | 5/2003 | DeGuillebon et al. | |
| 6,616,669 B2 | 9/2003 | Ogilvie et al. | |
| 6,656,179 B1 | 12/2003 | Schaefer et al. | |
| 6,656,185 B2 | 12/2003 | Gleason et al. | |
| 6,682,533 B1 | 1/2004 | Dinsdale et al. | |
| 6,689,140 B2 | 2/2004 | Cohen | |
| 6,723,335 B1 | 4/2004 | Moehlenbruck et al. | |
| 6,746,452 B2 * | 6/2004 | Tuke et al. | 606/91 |
| 6,773,438 B1 | 8/2004 | Knodel et al. | |
| 6,946,000 B2 | 9/2005 | Senegas et al. | |
| 7,481,828 B2 | 1/2009 | Mazda et al. | |
| 7,699,874 B2 | 4/2010 | Young | |
| 7,959,654 B2 | 6/2011 | Mazda | |
| 2002/0116013 A1 | 8/2002 | Gleason et al. | |
| 2002/0198538 A1 | 12/2002 | Kortenbach et al. | |
| 2004/0087979 A1 | 5/2004 | Field et al. | |
| 2004/0097942 A1 | 5/2004 | Allen et al. | |
| 2004/0138666 A1 | 7/2004 | Molz, IV et al. | |
| 2005/0070958 A1 | 3/2005 | Swayze et al. | |
| 2005/0085815 A1 | 4/2005 | Harms | |
| 2005/0131404 A1 | 6/2005 | Mazda | |
| 2005/0154403 A1 | 7/2005 | Sauer et al. | |
| 2005/0228375 A1 | 10/2005 | Mazda et al. | |
| 2005/0273983 A1 | 12/2005 | Mattchen | |
| 2006/0235387 A1 | 10/2006 | Peterman | |
| 2006/0235391 A1 | 10/2006 | Sutterlin, III | |
| 2007/0088359 A1 | 4/2007 | Woods et al. | |
| 2007/0299445 A1 | 12/2007 | Shadduck et al. | |
| 2008/0033557 A1 | 2/2008 | Pasquet et al. | |
| 2008/0125780 A1 | 5/2008 | Ferree | |
| 2008/0140133 A1 | 6/2008 | Allard et al. | |
| 2008/0208256 A1 | 8/2008 | Thramann | |
| 2009/0131985 A1 | 5/2009 | Mazda | |
| 2009/0138048 A1 * | 5/2009 | Baccelli et al. | 606/263 |

FOREIGN PATENT DOCUMENTS

| | | |
|---|---|---|
| EP | 0780096 | 6/1997 |
| EP | 1815812 | 8/2007 |
| FR | 522040 | 7/1921 |
| FR | 26156 | 9/1923 |
| FR | 2704745 | 11/1994 |
| FR | 2722088 | 1/1996 |
| FR | 2799948 A1 | 4/2001 |
| FR | 2817929 | 6/2002 |
| FR | 2867057 | 9/2005 |
| FR | 2870718 | 12/2005 |
| FR | 2890850 | 3/2007 |
| FR | 2890851 | 3/2007 |
| FR | 2897771 A1 | 8/2007 |
| GB | 2269753 | 2/2004 |
| JP | 2001299770 | 10/2001 |
| WO | WO9416635 A1 | 8/1994 |
| WO | WO0207621 A1 | 1/2002 |
| WO | WO0207622 A1 | 1/2002 |
| WO | WO0209604 A1 | 2/2002 |
| WO | WO0217803 A2 | 3/2002 |
| WO | WO02051326 A1 | 7/2002 |
| WO | WO02071960 A1 | 9/2002 |
| WO | WO 03007829 A1 | 1/2003 |
| WO | WO03103519 A1 | 12/2003 |
| WO | WO2004010881 A1 | 2/2004 |
| WO | WO 2005020860 A3 | 3/2005 |
| WO | WO2005120277 A1 | 12/2005 |
| WO | WO2006034423 A2 | 3/2006 |
| WO | WO 2006106268 A3 | 10/2006 |
| WO | WO 2006106246 | 12/2006 |
| WO | WO 2007023240 A3 | 3/2007 |
| WO | WO2007034112 A1 | 3/2007 |
| WO | WO2007036657 | 4/2007 |
| WO | WO2007099258 A2 | 9/2007 |
| WO | WO2009130276 A1 | 10/2009 |
| WO | WO2009141393 A1 | 11/2009 |

OTHER PUBLICATIONS

English Translation of International Preliminary Report for PCT/FR2006/050898 on Patentability Chapter I dated Apr. 29, 2008, 6 pages.

English Translation of International Preliminary Report on Patentability Chapter I for PCT/FR2006/050909, dated Apr. 8, 2008, 5 pages.

English Translation of the Written Opinion of the International Search Authority for PCT/FR2006/050909, dated Apr. 2, 2008, 4 pages.

English Translation of the Written Opinion of the International Search Authority for PCT/FR2006/050898, dated Apr. 28, 2008, 5 pages.

European Search Report for EP 08305183, dated Mar. 19, 2009, 10 pages.

European Search Report for EP 08305326, dated Nov. 12, 2008, 3 pages.

European Search Report for EP 2052689, dated Apr. 15, 2008, 6 pages.

European Search Report issued in EP 08305326 on Nov. 18, 2006, 3 pages.

French Preliminary Search Report and Written Opinion for FR200650609, dated Jun. 30, 2006, 5 pages.

International Search Report for WO2009053423, dated May 19, 2009, 1 page.

International Search Report for PCT/EP2008/063682, mailed Nov. 24, 2008, 3 pages.

International Search Report for PCT/FR2006/050909 published as WO/2007/034112, dated Jan. 24, 2007, 3 pages.

Office Action for U.S. Appl. No. 10/521,914, dated Dec. 29, 2006, 21 pages.

Office Action for U.S. Appl. No. 10/521,914, dated Mar. 19, 2008, 7 pages.

Office Action for U.S. Appl. No. 10/521,914, dated Jun. 16, 2006, 13 pages.

Office Action for U.S. Appl. No. 10/521,914, dated Jul. 30, 2007, 13 pages.

International Search Report and Written Opinion for PCT/US2009/038977, mailed Jul. 22, 2009, 13 pages.

Korean Examination report for Korean Patent Application No. 1020057001238, mailed Feb. 23, 2010, 3 pages.

French Preliminary Search Report for FR0209317, dated Apr. 9, 2003, 1 page.

French Preliminary Search Report for FR0509629, mailed Jun. 9, 2006, 2 pages.

International Search Report for PCT/FR2003/02307, dated Jan. 2, 2004, 2 pages.

Australian Search Report for Australian Patent Application No. 2003267529, dated Nov. 15, 2007, 2 pages.

French Preliminary Search Report for FR0509570, dated Jun. 29, 2006, 2 pages.

International Search Report for PCT/FR2006/050898, dated Feb. 2, 2007, 2 pages.

Written Opinion for PCT/US2009/038977, mailed Feb. 24, 2010, 7 pages.

European Search Report for European Patent Application No. 07 301 454.0, mailed Sep. 25, 2008, 8 pages.

Partial European Search Report issued in European Application No. 07 301 483.9, completed Apr. 15, 2008, mailed Apr. 23, 2008, 6 pages.

European Search Report and Search Opinion issued in European Application No. 07 301 483.9, completed Apr. 15, 2008, mailed Jul. 10, 2008, 10 pages.

International Search Report and Written Opinion issued in PCT Application No. PCT/EP2008/064344, completed Jan. 16, 2009, mailed May 19, 2009, 11 pages.
International Search Report and Written Opinion for PCT Application No. PCT/EP2008/062791, completed Nov. 18, 2008, mailed Dec. 4, 2008, 10 pages.
French Preliminary Search Report for French Application No. 0757814, issued May 22, 2008, 2 pgs.
International Preliminary Report on Patentability issued in International Patent Application No. PCT/EP2008/062791, Mar. 30, 2010, 7 pages.
International Preliminary Report on Patentability issued in International Patent Application No. PCT/EP2008/063682, Apr. 13, 2010, 8 pages.
International Preliminary Report on Patentability issued in International Patent Application No. PCT/EP2008/064344, Apr. 27, 2010, 8 pages.
International Preliminary Report on Patentability issued in International Patent Application No. PCT/US2009/038977, May 27, 2010, 12 pages.
French Preliminary Search Report in French Patent Application No. FR 0405611, dated Jan. 12, 2005, 2 pages.
International Search Report issued in International Patent Application No. PCT/FR2005/001280, Nov. 7, 2005, 3 pages.
Written Opinion for International Patent Application No. PCT/FR2005/001280, Nov. 25, 2006, 5 pages.
International Search Report and Written Opinion issued in International Patent Application No. PCT/EP2008/063682, mailed Nov. 24, 2008, 11 pages.
International Search Report and Written Opinion issued in International Patent Application No. PCT/FR2006/050909, published as WO/2007/034112, mailed Jan. 24, 2007, 10 pages.
Office Action issued in U.S. Appl. No. 12/358,748, mailed Sep. 15, 2010, 7 pages.
Office Action issued in U.S. Appl. No. 11/996,918, mailed Feb. 14, 2011, 12 pages.
Office Action issued in U.S. Appl. No. 12/059,634, mailed Feb. 15, 2011, 14 pages.
Office Action issued in U.S. Appl. No. 12/408,592, mailed Feb. 18, 2011, 17 pages.
Notice of Allowance issued in U.S. Appl. No. 12/358,748, mailed Feb. 23, 2011, 5 pages.
Office Action issued in U.S. Appl. No. 12/059,634, mailed Jun. 22, 2011, 15 pages.
European Search Report issued in European Patent Application No. EP08305124.3, Oct. 24, 2008, 4 pages.
Office Action issued in U.S. Appl. No. 11/996,918, mailed Aug. 17, 2011, 11 pages.
Notice of Allowance issued in U.S. Appl. No. 12/375,265, mailed Aug. 25, 2011, 10 pages.
Office Action issued in U.S. Appl. No. 12/408,592, mailed Sep. 22, 2011, 24 pages.
Office Action issued in U.S. Appl. No. 12/059,634, mailed Oct. 5, 2011, 12 pages.

* cited by examiner

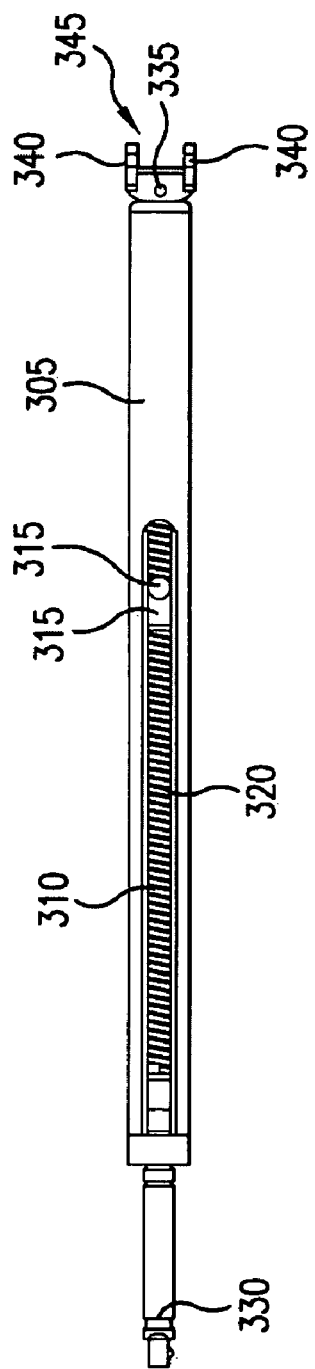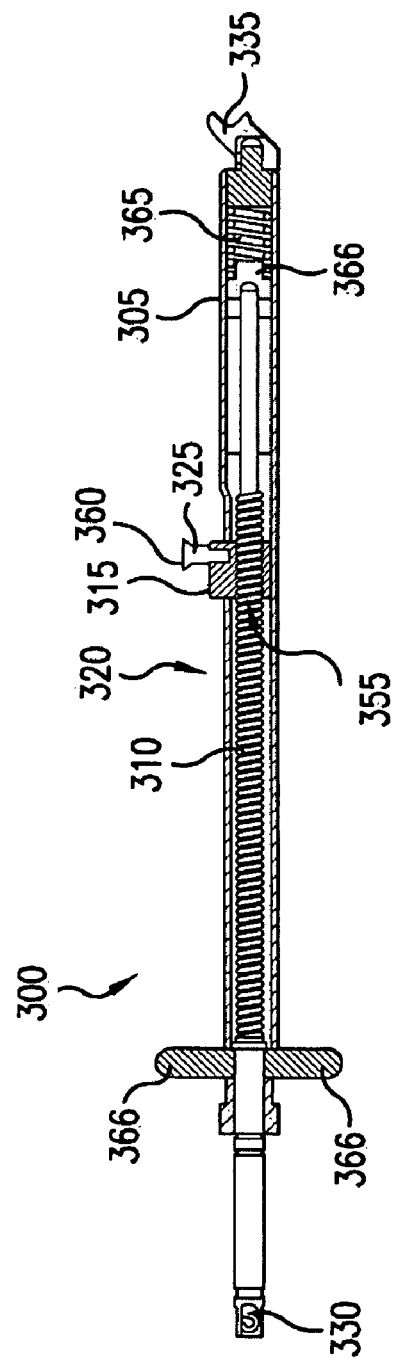

BONE FIXATION TENSIONING TOOL AND METHOD

TECHNICAL FIELD OF THE DISCLOSURE

This disclosure relates generally to systems and method for fixing bone. In particular, embodiments of the disclosure may be helpful for holding bones, rods, or other structures in a desired configuration or in particular relative position. Even more particularly, the disclosure relates to instruments and methods for installing bone fixing systems.

BACKGROUND OF THE DISCLOSURE

The spine is formed of superposed vertebrae, normally aligned along a vertebral axis, from the lumbar vertebrae to the cervical vertebrae, each having a posterior wall from which projects a spinous process and two lateral edges from the walls of which there project ribs and/or transverse processes. If the spine of a person has abnormal curvature, the vertebrae are typically inclined relative to one another and relative to said vertebral axis. The lateral edges of the vertebrae on one side are therefore closer together and form a concave shape while the lateral edges on the other side are farther apart and form a convex shape.

In order to straighten the vertebral column as a remedy for this situation, the lateral edges of the vertebrae on the concave side can be moved away from one another and supported at distances from one another substantially equivalent to the distances between the lateral edges on the other side. Devices known in the art to hold the vertebrae relative to one another include screws that are inserted into the vertebrae or hooks that are inserted along the internal wall of the spinal canal and rods adapted to connect the screws or hooks.

When using a hook and rod system, pairs of hooks are generally inserted into each vertebra, one on each side, near the pedicle. The hooks typically have heads that project from the posterior wall of the vertebra, one on each side of the spinous process. The heads can be tulip-shaped and adapted to receive a rod that is immobilized by a nut screwed onto the head and contacting the rod. The heads of the hooks situated on either side of the spinous process can then be connected together and fixed in position by two rods approximately parallel to one another and to the axis of the spine.

However, using such hooks can be difficult because their use increases the risk that the physician (or other operative) might contact and potentially damage the spinal cord that extends along the center of the spinal canal (which can result in paralysis of the patient).

Using a screw and rod system reduces this risk, but has other drawbacks. The screws typically have tulip-shaped heads and are inserted in pairs into the pedicles on each side of the spinous process on the posterior wall of the vertebrae. The screws therefore constitute fixing points on the vertebrae for holding the vertebrae in a fixed position relative to one another. However, the screws are inserted into the pedicles of the vertebrae, which in some cases are small or have deteriorated and can be damaged or do not provide sufficient purchase to permanently hold the screw.

SUMMARY OF THE DISCLOSURE

According to various embodiments described herein, a surgical procedure can be performed using a tensioning tool that provides continuous control over tensioning the ligature. A user can form a loop about one or more structures in a patient's body with a conformable ligature and a ligature capturing implant. The ligature capturing implant can be a ligature capturing implant that include rods, compression members or can be another type of ligature capturing implant. The structures can include, for example, a bone, a bone fastener, a tendon, a bone graft, a plate, a rod or other structure in the body. The user can attach a portion of the conformable ligature to a tensioning member of a tensioning tool that provides a continuous range of control. The tensioning tool can comprise a first portion in threaded engagement with a second portion. For example, the tensioning tool can comprise a drive shaft that engages with a carriage, a column that engages with a threaded shaft, a threaded shaft that engages with another shaft or other threaded portions that engage with each other to translate rotational motion of the portions relative to each other into linear motion of the tensioning member. The user can rotate the first portion relative to the second portion to move the tensioning member to tension the loop. For example, a user can rotate a drive shaft to move a carriage carrying the tensioning member. In some embodiments, the user can disengage the carriage from the drive shaft and slide the carriage along the drive shaft to a selected position. As another example, the user can rotate one portion of the tool to move a shaft that is coupled to the tensioning member. The first portion can also be rotated relative to the second portion in an opposite direction to release tension from the loop.

According to one embodiment, a spinal reduction can be performed using tensioning tools. A method of progressive spinal reduction can comprise forming multiple loops about structures in a patient's body with multiple conformable ligatures and ligature capturing implants and partially tensioning each conformable ligature in turn with a corresponding tensioning tool until each conformable ligature is at a desired tension to perform spinal reduction procedure. Tensioning each conformable ligature may comprise attaching a portion of that conformable ligature to a tensioning member of the corresponding tensioning tool, the corresponding tensioning tool comprising a first portion in threaded engagement with a second portion and rotating the first portion relative to the second portion to move the tensioning member away from a corresponding ligature capturing implant to tension that conformable ligature about at least a portion of a vertebra. The first portion is rotated relative to the second portion about an axis that is substantially parallel to a primary direction of movement of the tensioning member.

Another embodiment of a method comprises providing a tensioning tool comprising, a tool body defining a slot, a threaded drive shaft running through at least a portion of the tool body, a tensioning member and a carriage coupled to the tensioning member. The carriage defines a drive shaft passage having at least one thread engaging portion to engage threads on the drive shaft. The drive shaft passes through the drive shaft passage. The method further comprises forming a loop about one or more structures in a patient's body with a conformable ligature and a ligature capturing implant and coupling a portion of the conformable ligature to the tensioning member. The method can further include rotating the drive shaft to move the carriage away from the ligature capturing implant to tension the conformable ligature. Embodiments can also include rotating the drive shaft the opposite direction to release tension from the loop. The structures about which the loop is formed can include, for example, a bone, a bone fastener, a tendon, a bone graft, a plate, a rod or other structure in the body.

According to one embodiment, the drive shaft passage includes one or more additional unthreaded portions. The method can further comprise rotating the carriage to disengage the at least one thread engaging portion from the threaded drive shaft and sliding the carriage along the drive shaft to a desired position.

Another embodiment of a method for holding a bone in a position, the method comprises passing a conformable ligature around one or more structures in a body, passing first and second ends of the conformable ligature through a loop passage in a ligature capturing implant to form a loop, adjusting the ligature capturing implant to increase to resistance on the movement of the conformable ligature to a selected amount that allows the conformable ligature to move through the ligature capturing implant when a force is applied to the conformable ligature, attaching a portion of the conformable ligature to a tensioning member of a tensioning tool, rotating a threaded drive shaft of the tensioning tool to move the tensioning member to apply tension to the conformable ligature and adjusting the ligature tensioning implant to prevent the loop from loosening. According to one embodiment, rotating a threaded drive shaft of the tensioning tool to move the tensioning member comprises rotating the threaded drive shaft to move a carriage coupled to the tensioning member. The carriage can define a drive shaft passage having at least one thread engaging portion to engage threads on the drive shaft and wherein the drive shaft passes through the drive shaft passage. The method can further comprise positioning the tensioning tool so that a connecting portion of the tensioning tool abuts the ligature capturing implant. According to one embodiment the drive shaft can be rotated in an opposite direction to release tension from the conformable ligature.

According to one embodiment a drive shaft passage can include one or more additional unthreaded portions. The method can further include rotating the carriage to disengage the at least one thread engaging portion from the threaded drive shaft and sliding the carriage along the drive shaft to a desired position.

Another embodiment comprises a tensioning tool providing continuous control of conformable ligature tension, the tensioning tool comprising a tool body defining a slot, a connection portion shaped to at least abut a ligature capturing implant, a threaded drive shaft running through at least a portion of the tool body, a tensioning member and a carriage coupled to the tensioning member, the carriage defining a drive shaft passage having at least one thread engaging portion to engage threads on the drive shaft and wherein the drive shaft passes through the drive shaft passage, wherein rotation of the drive shaft causes the carriage to move towards or away from the connection portion. According to one embodiment, the carriage is configured to be rotated from a first position in which the at least one thread engaging portion is engaged with threads on the drive shaft to a second, slidable position, in which the at least one thread engaging portions is not engaged with the threads of the drive shaft.

The tensioning tool can further comprise a drive shaft seat in which a first end of the drive shaft is seated, a spring that compresses between the drive shaft seat of and the tool body, and a removable handle connected to a second end of the drive shaft distal from the first end.

Embodiments of the disclosed systems and methods can provide the advantage of providing progressive and continuous tensioning of a ligature used in bone fixing procedures.

Embodiments of the disclosed systems and methods can provide the advantage of allowing tension of the ligature to be progressively reduced in an easily controlled manner.

Embodiments of the disclosed systems and methods provide another advantage by allowing a tensioning tool used to tension one ligature to be left in place while the other ligatures are tightened.

BRIEF DESCRIPTION OF THE FIGURES

FIG. 40 is a diagrammatic representation of another embodiment of tensioning tool.

FIG. 41 is a cross sectional view of one embodiment of a tensioning tool.

DETAILED DESCRIPTION

Figure 1:
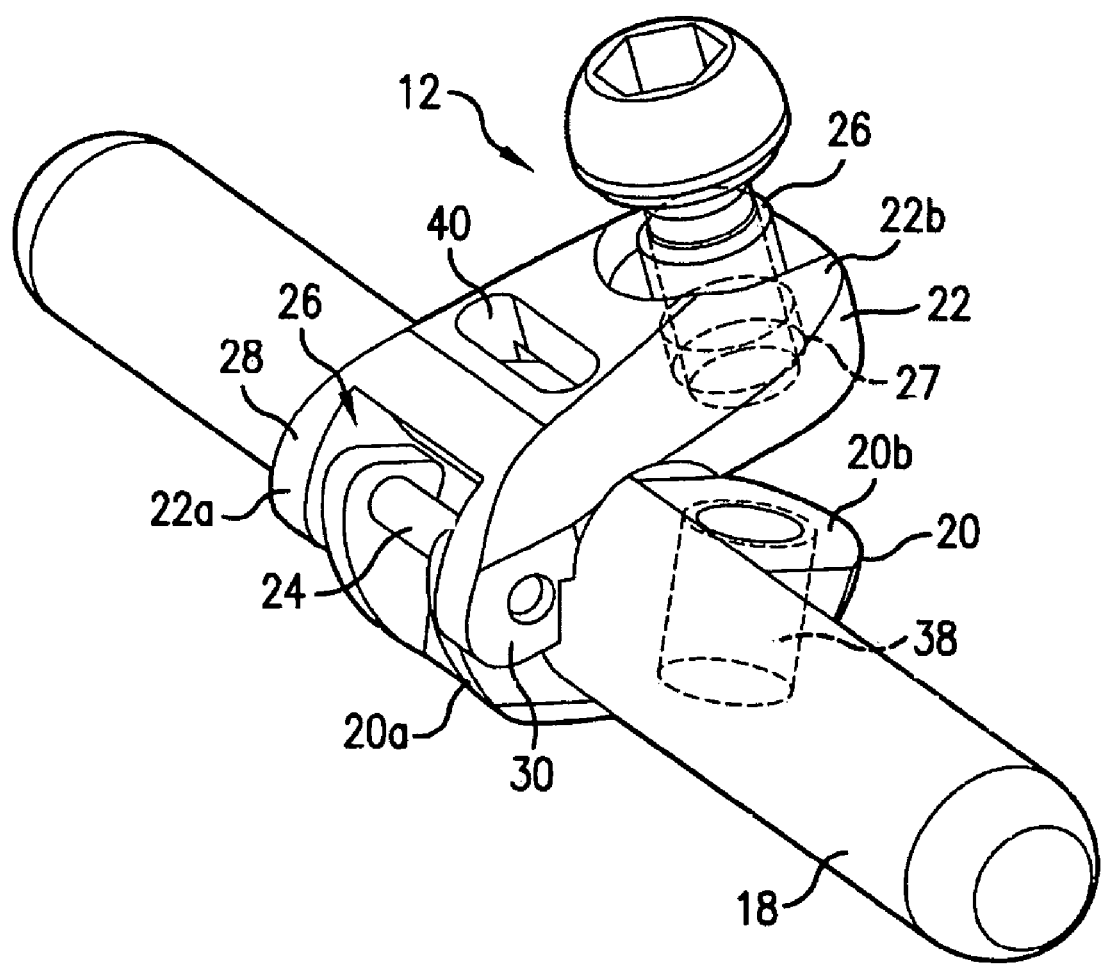
FIG. 1 is a fragmentary diagrammatic perspective view showing a vertebral fixing system of the disclosure and a rod.

The disclosure and the various features and advantageous details thereof are explained more fully with reference to the non-limiting embodiments that are illustrated in the accompanying drawings and detailed in the following description. Descriptions of well known starting materials, processing techniques, components and equipment are omitted so as not to unnecessarily obscure the disclosure in detail. Skilled artisans should understand, however, that the detailed description and the specific examples, while disclosing preferred embodiments of the disclosure, are given by way of illustration only and not by way of limitation. Various substitutions, modifications, additions or rearrangements within the scope of the underlying inventive concept(s) will be apparent to those skilled in the art after reading this disclosure.

A bone fixing system may be installed in a patient to hold or fix one structure in a selected relation with one or more other structures. As used herein, the term structure may refer to bones, portions of bones, or bone implants, as well as rods, elongated members, plates, or other implanted man-made devices. Among other methods, a bone fixing system as described herein may be installed using a minimally invasive surgery (MIS) procedure. In one embodiment, the bone fixing system and method of use may include instruments and bone fixing components for maintaining one or more structures in a selected alignment.

Components of bone fixing systems in accordance with the disclosure may be made of materials including, but not limited to, titanium, titanium alloys, stainless steel, ceramics, and/or polymers. Some components of a bone fixing system may be autoclaved and/or chemically sterilized. Components that may not be autoclaved and/or chemically sterilized may be made of sterile materials. Components made of sterile materials can be used with other sterile components during assembly of a bone fixing system.

Embodiments of bone fixing systems disclosed herein are useful in repairing broken bones, correcting curvatures of the spine and for other surgical procedures that hold structures (e.g., bones) in a fixed relative position. Embodiments of the bone fixing system and method of use disclosed herein can be particularly useful for minimally invasive surgery (MIS) procedures, which can reduce trauma to soft tissue due to the relatively small incision made in a patient. For example, a surgical procedure may be performed through a 2 cm to 4 cm incision formed in the skin of the patient. Dilators, a targeting needle, and/or a tissue wedge may be used to provide access to structures without the need to form a larger incision with a scalpel through muscle and other tissue. A minimally invasive surgery (MIS) procedure may reduce an amount of post-operative pain felt by a patient as compared to invasive procedures. A minimally invasive procedure may also reduce recovery time for the patient as compared to invasive procedures. In some embodiments, the natural flexibility of skin and soft tissue may be used to limit the length and/or depth of an incision or incisions needed during the procedure. Minimally invasive procedures may provide limited direct visibility in vivo.

Bone fixing systems may be used to correct problems due to spinal injury, deformity, or disease. For example, various embodiments of a bone fixing system may be used from the C1 vertebra to the sacrum to correct spinal problems. For example, a bone fixing system may be implanted posterior to the spine to maintain distraction between adjacent vertebral bodies in a lumbar portion of the spine. Various embodiments of a bone fixing system may be used to correct orthopedic deficiencies. Embodiments of the disclosure may be useful for holding tendons, bones, or muscles during the healing process and may be implanted using MIS procedures and thus it is in this context that embodiments of the disclosure may be described. It will be appreciated, however, that embodiments of the systems and methods of the present disclosure may be applicable for stabilizing other areas of the body.

In general, a flexible ligature can be used to secure bones or other structures. The ligature comprises an elongate flexible member capable of conforming to the contour of the parts that it connects. The ligature can be passed through a ligature capturing implant to form a loop that is looped about the structures to fixed relative to each. The ligature capturing implant can be any body through which the ligature passes to form a loop and that allows the loop to be tightened and left in a patient's body in a tightened state. According to one embodiment, force is applied to the ligature to tension the loop. The instrument used to tighten the ligature can include a first shaft, a second shaft drivably engaged with the first shaft and a tensioning member. The tensioning member can be coupled to the first shaft or the second shaft or can be drivably engaged with one or both of the first shaft and the second shaft. A portion of the ligature couples to the tensioning member such that movement of tensioning member can increase the tension in the ligature. For example, a portion of the ligature can be formed into a loop that is looped around the tensioning member. Movement of the tensioning member can be driven by rotational movement of the first shaft relative to the second shaft. Embodiments of an instrument tensioning the ligature are discussed below in conjunction with FIGS. 40-44.

By way of context, FIG. 1 shows one embodiment of a bone fixing system, specifically a vertebral fixing system 10 of the disclosure mounted on a rod 18. The vertebral fixing system comprises a connecting part 12 having two longitudinal members, of which a first longitudinal member 22 extends between a first end 22a and a second end 22b and a second longitudinal member 20 extends between a first end 20a and a second end 20b. The two longitudinal members 22 and 20 are pivoted together at their first ends 20a and 22a for the purposes of mounting the system. The first end 22a of the longitudinal member 22 has a notch 26 with two opposite edges 28 and 30 and between which the first end 20a of the other longitudinal member 20 may be inserted. A pivot pin 24 passes through the two first ends 20a and 22a and is free to rotate in at least one of said ends 20a and/or 22a. The second end 22b of the first longitudinal member 22 includes a bore 28 into which a screw 26 may be inserted. The second end 20b of the second longitudinal member 20 comprises a thread 38 which is aligned with said bore 28 when the two longitudinal members are disposed facing each other, with the result that the screw 26 may be screwed into said thread 38 in order to drive the second ends 20b and 22b of the two longitudinal members 20 and 22 towards each other. The consequences of screwing said screw 26 into the thread 38, thereby forming the adjustable locking means, are explained in more detail hereinafter FIG. 1 also shows a first orifice 40 through which a ligature may be stretched. The method of connecting said ligature to said connecting part is described with reference to FIG. 2.

Figure 2:
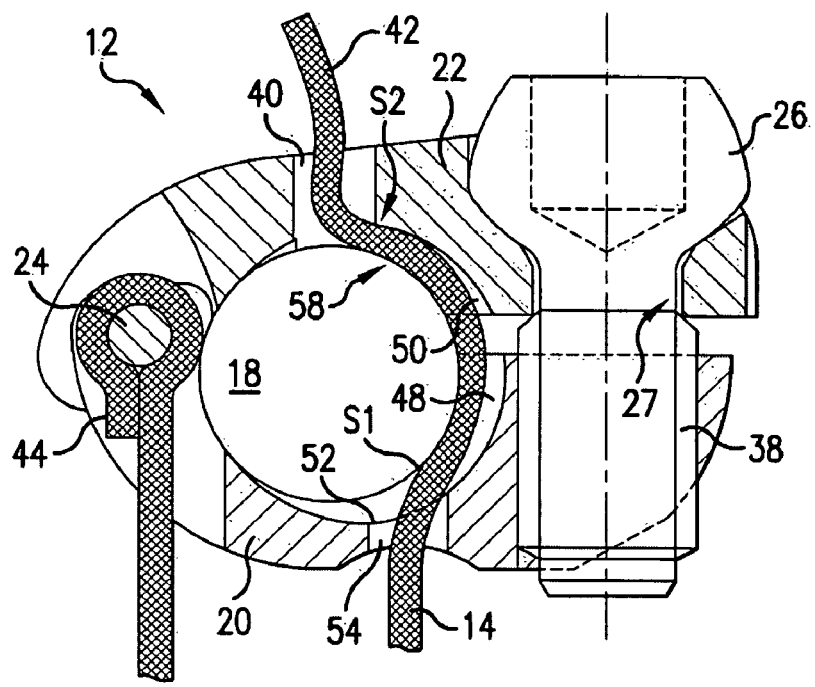
FIG. 2 is a diagrammatic view in vertical section of the subject matter of the disclosure mounted on a rod.

FIG. 2 shows the connecting part 12 comprising of the first longitudinal member 22 and the second longitudinal member 20, said longitudinal members 22 and 20 pivoting about the pin 24 that joins them. The adjustable locking means comprising of said screws 26 passing through the bore 28 and screwed into the thread 38 to immobilize said connecting part 12 relative to the rod 18 and fix in position a portion of a ligature 14 shown in part in FIG. 2.

The ligature 14 consists of an elongate flexible member capable of conforming to the contour of the parts that it must connect.

Figure 4:
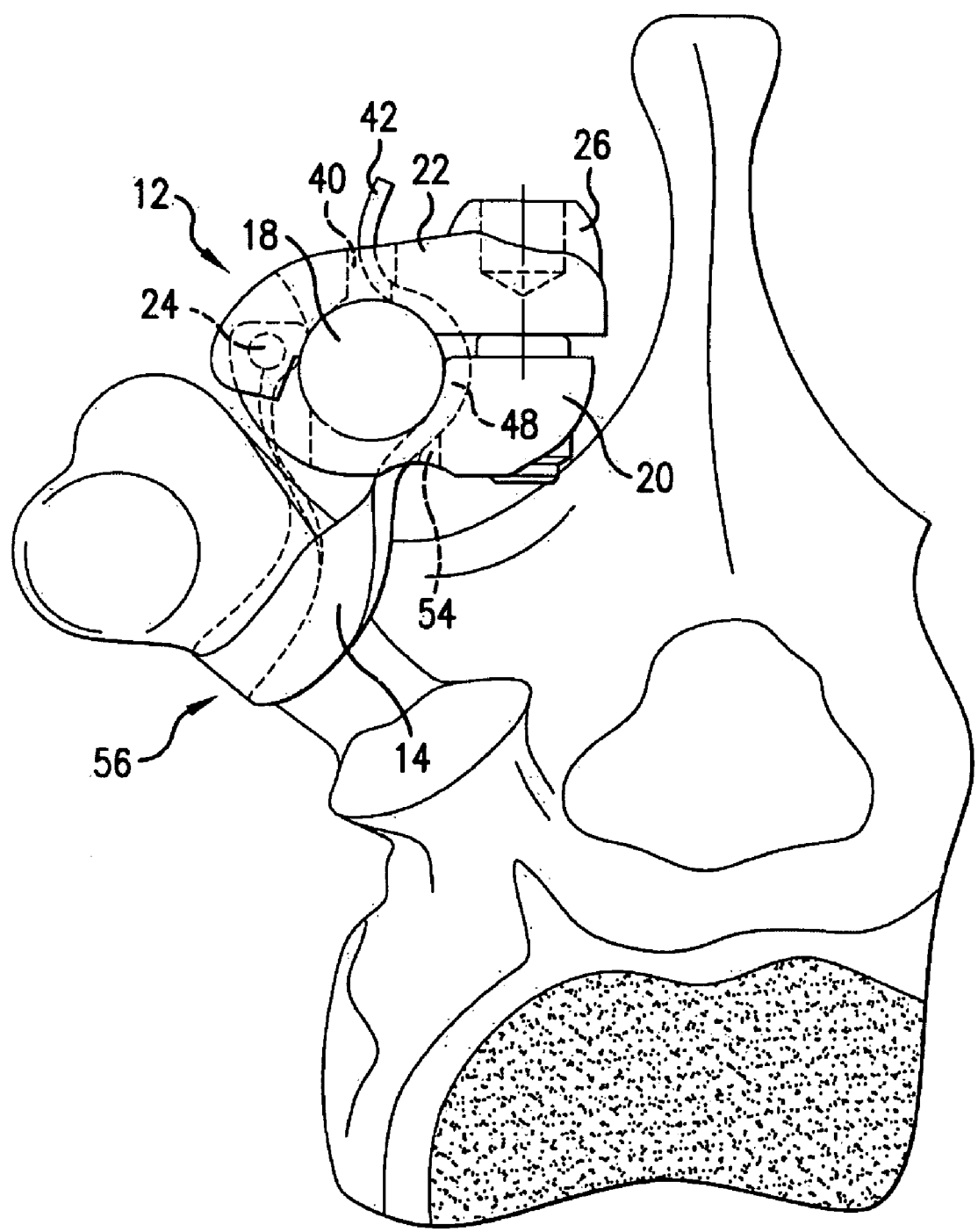
FIG. 4 is a diagrammatic view in elevation of the subject matter of the disclosure mounted on a vertebra.

The ligature 14 has a first end 44 that is ligated around the pin 24 and a free second end 42 that is inserted into a passage 48 between the rod 18 and the internal walls 50 and 52 of the longitudinal members 22 and 20 and the external wall of the rod 18. As shown in FIG. 2, the second longitudinal end 20a includes a second orifice 54 through which said ligature 14 passes. Moreover, as shown in FIG. 4, the ligature 14 may be formed into a loop 56 in which the transverse process is trapped. In some embodiments, the ligature 14 may also trap the rib.

Figure 3:
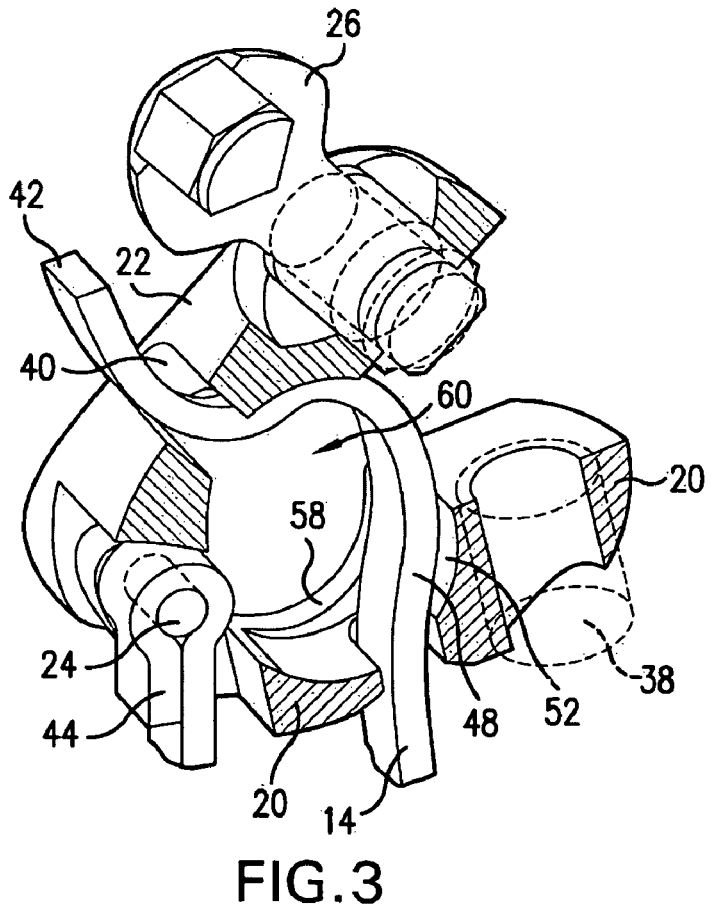
FIG. 3 is a diagrammatic perspective view in section of the subject matter of the disclosure.

As shown in FIG. 3, which shows the second longitudinal member 20, the middle part has a first portion through which said ligature 14 passes and a second portion 58 adapted to bear directly on the rod 18. In some embodiments, the passage 48, which is symmetrical inside the first longitudinal member 14, is produced by a groove formed in each of the two facing faces of the middle parts of the longitudinal members 22 and 20.

In some embodiments, the first portion of the middle part forms an edge with cylindrical symmetry and that the corresponding second portion of the middle part 58 of the first longitudinal member 22 forms a substantially cylindrical space 60 into which said rod 18 is inserted.

FIG. 2 shows that the second portion 58 of the middle part comes into contact with the rod 18 and is adapted to bear on top of it and the first portion presses the free second end of said ligature 14 against the rod 18. The adjustable locking means therefore drive the longitudinal members 22 and 20 forcibly against the rod 18 and simultaneously against the ligature 14, which is also forcibly pressed against the rod 18.

In some embodiments, as shown in FIG. 2, the passage 48 has a section S1 in the vicinity of the orifice 54 greater than the section S2 in the vicinity of the first orifice 40, the section of said passage 48 decreasing progressively in the direction from the second orifice 54 to the first orifice 40. The ligature 14 is therefore progressively compressed around a portion of the rod 18 with a pressure that increases in the direction from the second orifice 54 towards the first orifice 40.

FIG. 4 shows a vertebral fixing system of the disclosure mounted on a vertebra having a transverse process. This figure shows again the rod 18 and the two longitudinal members 22 and 20 that grip it and press a portion of the ligature 14 against said rod 18.

In FIG. 4, the flexible ligature 14 consists of a flexible strip of substantially constant width and thickness whose first end is ligated to the pin 24, the ligature 14 surrounding the transverse process of the vertebra being inserted through the connecting part 12. The section of the flexible strip 14 is substantially rectangular so that, the pin 24 and the rod 18 being substantially perpendicular to the transverse process, the ligature 14 has to be partly twisted in order to insert it into the passage 48 and between the pin 24 and the point at which it contacts the transverse process. The connecting part 12 is fixed in position against the posterior wall of the vertebra despite these partially twisted portions, the ligature 14 being forcibly tensioned by stretching the free second end 14.

The ligature 14 is advantageously made from a flexible material such as polyester that may be lightly crushed locally to immobilize it with a clamping effect.

One aspect of the disclosure relates to a spine straightening assembly comprising a plurality of vertebral fixing systems conforming to the present disclosure and mounted on a plurality of successive vertebrae, on all the transverse processes of one lateral wall thereof, and connected to a single rod that is disposed substantially parallel to said spine. The transverse processes of a portion of the spine can therefore be connected together by a single longitudinal rod, to fix them in position relative to each other, by means of the above vertebral fixing system.

Figure 5:
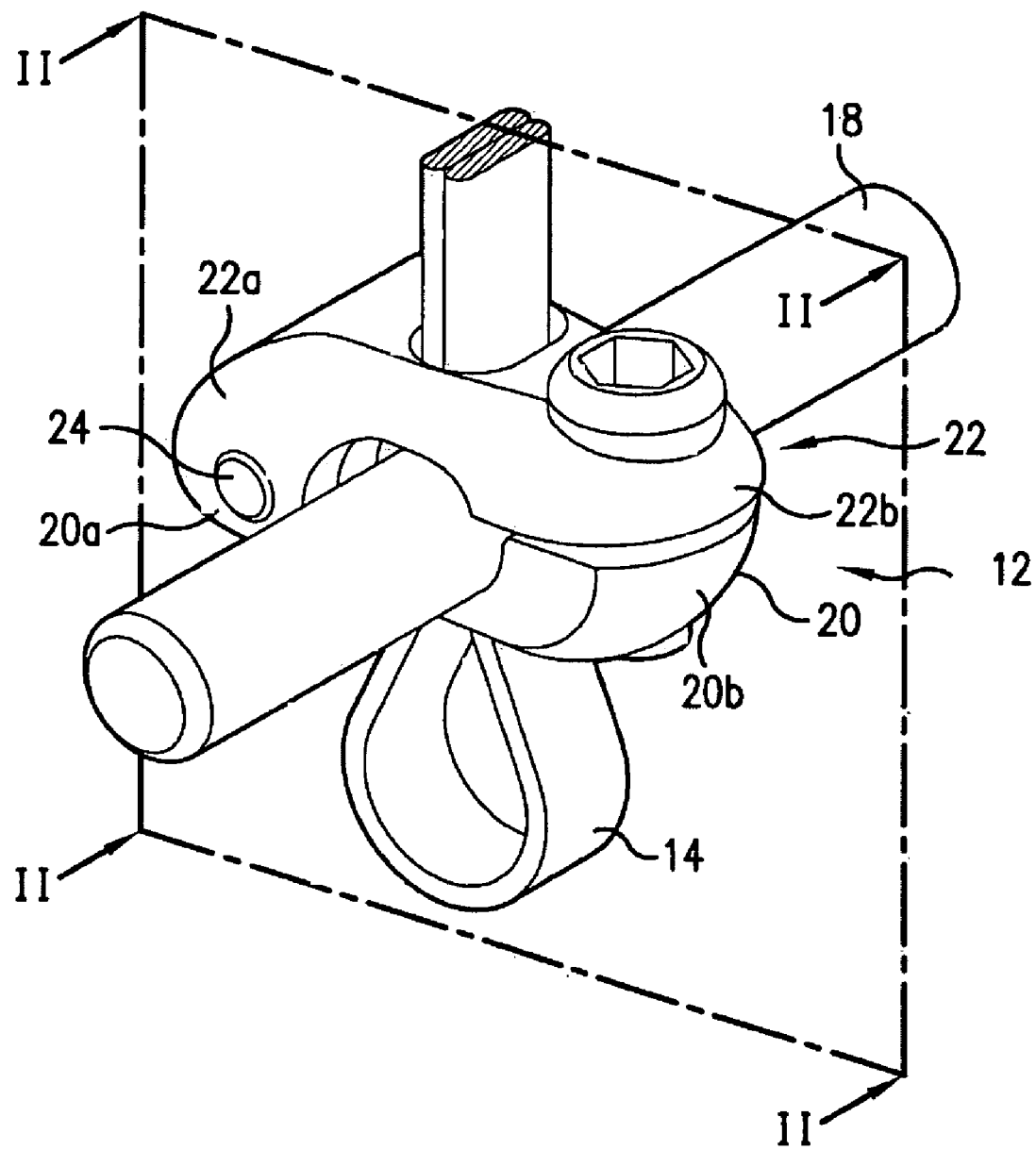
FIG. 5 is a perspective view of a first embodiment of a vertebral fixing system.

In some embodiments, flexible ligature 14 may not be ligated around pin 24 or otherwise fixed to connecting part 12. As shown in FIG. 5, in one embodiment, a vertebral fixing system comprises a connecting part 12, a flexible ligature 14, and adjustable locking means 16. The flexible ligature 14 is of elongate shape and is capable of matching the outline of the parts it is to connect together. In this figure, there can also be seen the rod 18 that is to be secured to the vertebra by means of the vertebral fixing system. In the first embodiment, the connecting part 12 is constituted by two longitudinal elements given respective references 22 and 20, each having a first end 22a, 20a and a second end 22b, 20b.

Figure 6A:
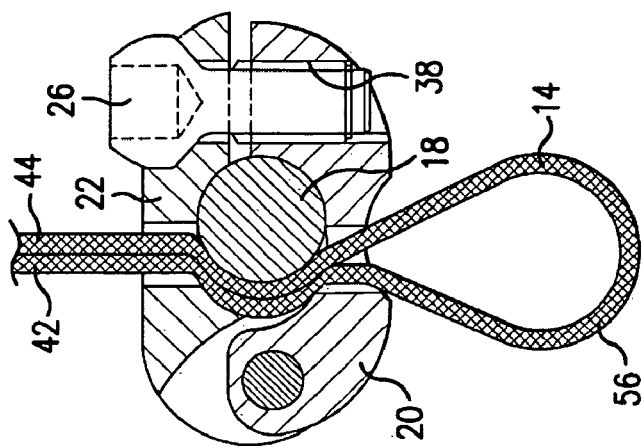
FIGS. 6A, 6B, and 6C are vertical section views of the fixing system showing the use of said system as shown in FIG. 5.

In FIG. 6A, the longitudinal elements 22 and 20 are hinged to each other at their second ends 22b, 20b about a pivot pin 24.

In the embodiment described, the locking means are constituted by a screw 26 having a head 26a that is engaged in a bore 28 formed in the first end 22a of the longitudinal element 22. The first end 20a of the longitudinal element 20 is pierced by a tapped bore 38 for co-operating with the threaded shank 26b of the screw 26. Each longitudinal element 20, 22 has an outside face 20c, 22c and an inside face 20d, 22d. The longitudinal elements 20 and 22 are mounted in such a manner that the inside faces 20d, 22d of the longitudinal elements face each other. The inside faces 20d, 22d of the longitudinal elements 20 and 22 have respective mutually-facing recesses 30 and 32, each of substantially semicylindrical shape. The recesses 30 and 32 define walls 34 and 36 which are ruled surfaces having generator lines parallel to the pivot axis 24. Finally, slots 54 and 40 cause the bottoms of the recesses 30 and 32 to communicate with the outside faces 20c and 22c of the longitudinal elements 20 and 22. As explained below, the recesses 30 and 32 are for receiving the rod 18 together with a strand of the ligature 14, the slots 54 and 40 serving to pass the ligature 14.

Figure 6B:
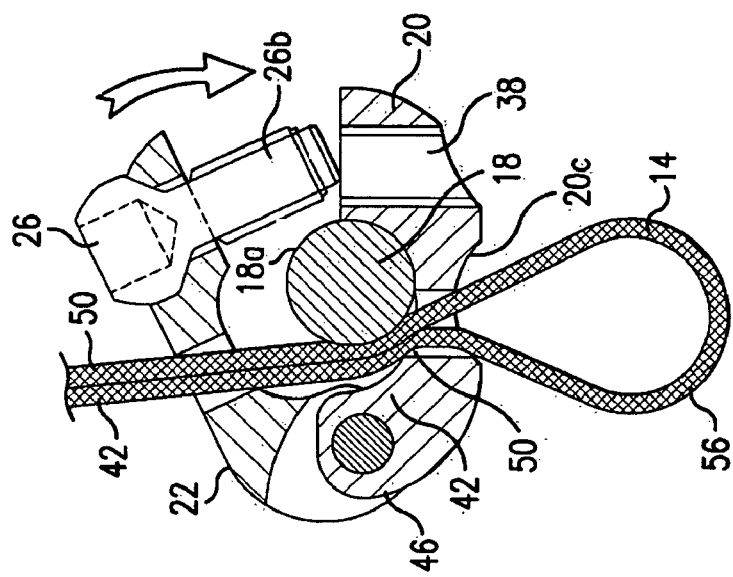
Figure 6C:
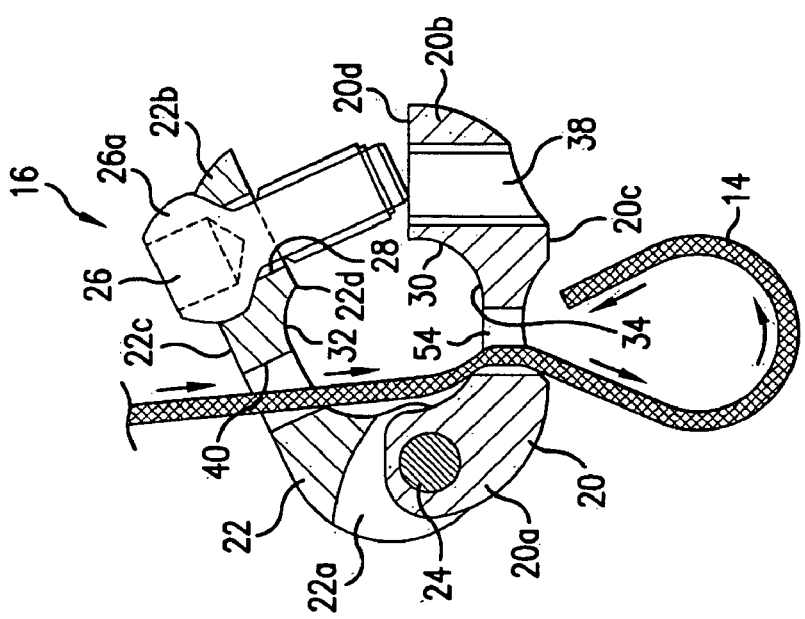

With reference to FIGS. 6A, 6B and 6C, there follows an explanation of how the fixing system is used.

In FIG. 6A, there can be seen the longitudinal elements 20 and 22 in the spaced-apart position, a position in which the locking means 16 are not active, the threaded shank 26b of the screw 26 not being engaged in the bore 38. The ligature 14 is engaged in the slots 54 and 40 of the longitudinal elements against one portion of the inside wall 34, 36 of the recesses 30 and 32. The rod 18 is then introduced into the recess 30 of the longitudinal element 20 so that the two strands 42 and 44 of the ligature 14 are disposed between the inside wall of the recesses 30 and 32 and the side face 18a of the rod 18. These two surfaces define a passageway 48 for passing the ligature 14 and having portions 42 and 44 of the ligature 14 placed therein.

As shown in FIG. 6B, the portions 42 and 44 of the ligature 14 define a portion of the ligature 14 that forms a loop that extends beyond the outside face 20c of the longitudinal element 20, and also two free portions 42 and 44 that extend beyond the outside face 22c of the longitudinal element 22. When the longitudinal elements 20 and 22 are spaced apart as shown in FIG. 6B, the ligature 14 can slide freely along the passageway 48. Once the ligature 14 is placed around the transverse process or a rib or indeed a portion of the posterior arc of a vertebra, the surgeon engages the threaded shank 26b of the screw 26 in the tapped bore 38, causing the longitudinal element 22 to come progressively closer to the longitudinal element 20. This approach simultaneously reduces the section of the passageway 48 in which the portions 42 and 44 of the ligature 14 are engaged and simultaneously introduces a certain coefficient of friction between the ligature and respectively the rod 18 and the walls of the recesses 30 and 32. Nevertheless, it is still possible for the surgeon to extract traction on the free ends 42 and 44 of the ligature 14 until sufficient tension is obtained in the ligature around the vertebral process. Once the tension in the ligature is sufficient for providing appropriate fastening, the surgeon finishes off tightening the screw 26 in the tapped bore 38, thus locking the longitudinal elements 20 and 22 together. Advantageously, the portions 42 and 44 of the ligature 14 are pinched between the rod 18 and the wall of the recesses 30 and 32.

In this locking position, the rod 18 is thus secured to the ligature 14 via the connecting part 12.

Figure 7:
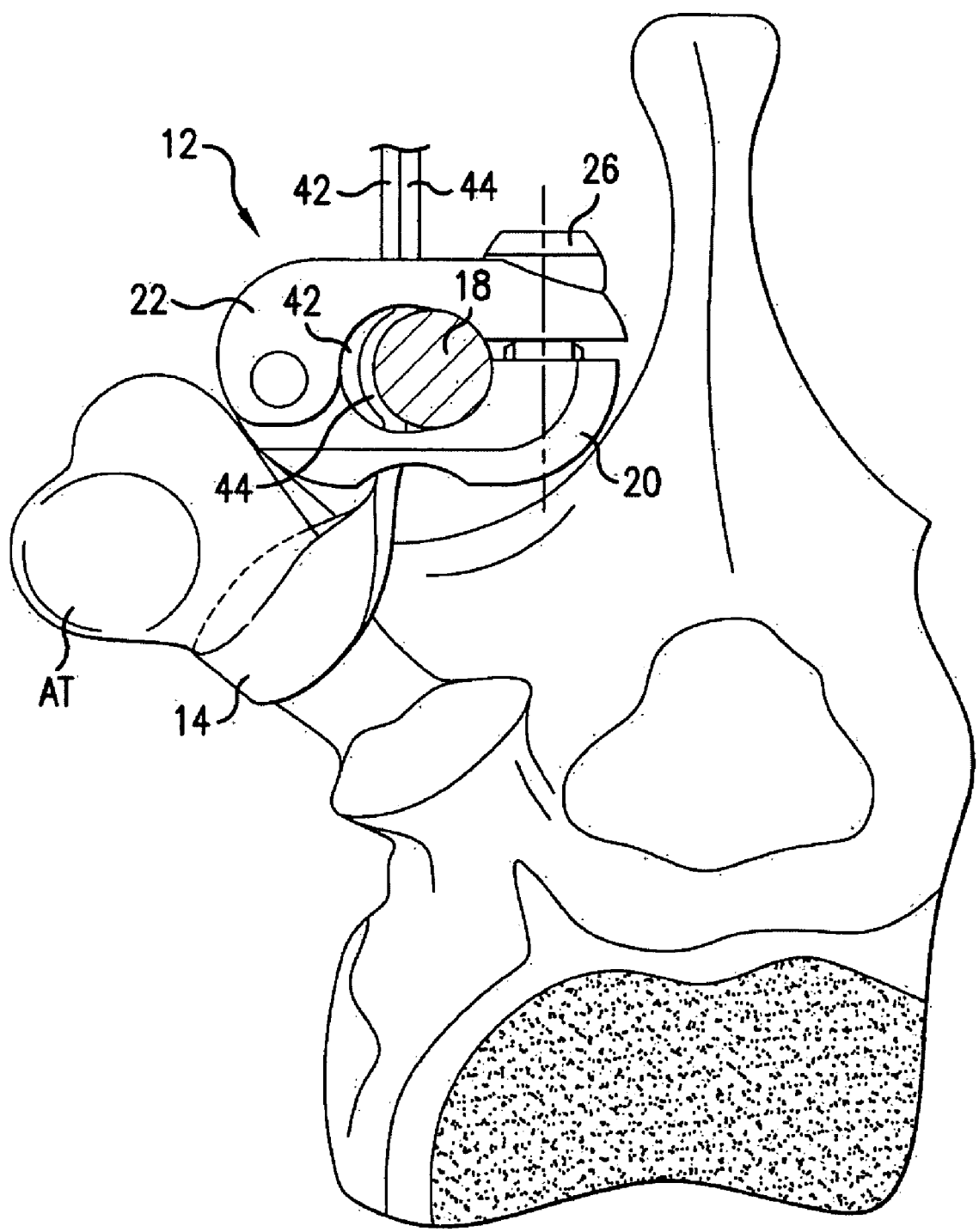
FIG. 7 is a face view showing the FIG. 5 fixing system put into place on a vertebra.
Figure 8:
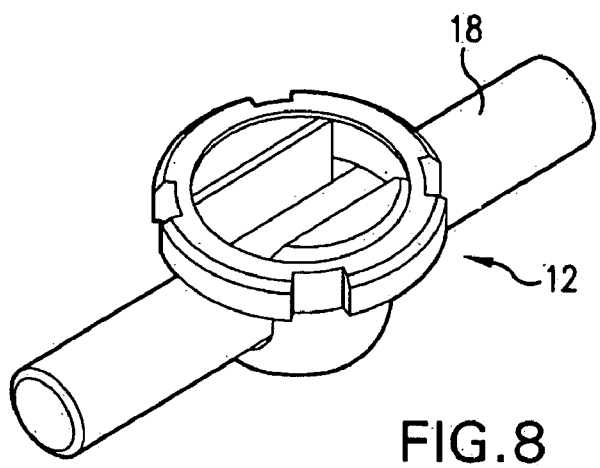
FIG. 8 is a perspective view of a second embodiment of the fixing system, the ligature not being shown.
Figure 9:
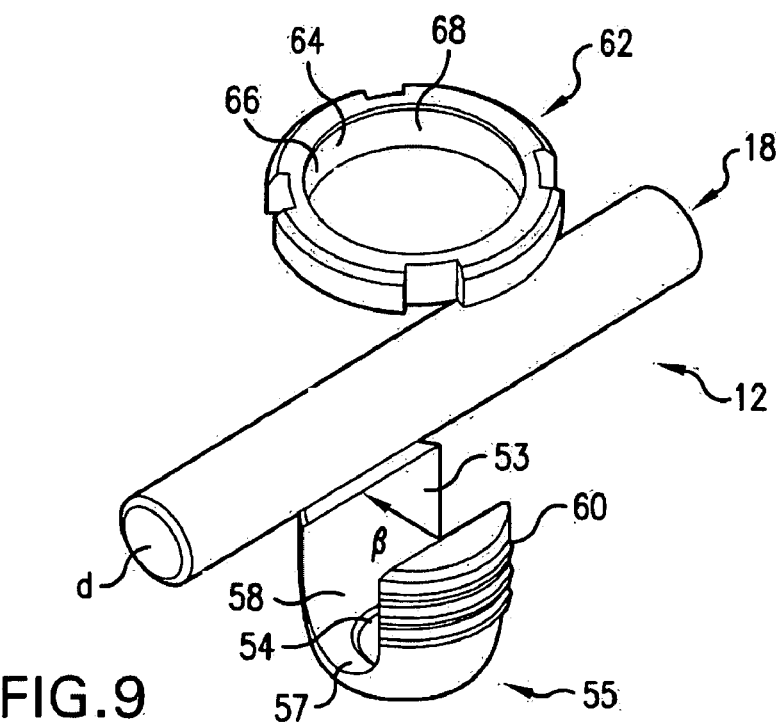
FIG. 9 is an exploded view of the connection device of FIG. 8.

Advantageously, because the surgeon exerts traction only on the free ends 42 and 44 of the ligature 14, there is no risk of jamming between the ligature 14 and the bottom face of the transverse process or of the rib, thus guaranteeing that effective fastening is provided with the transverse process or the rib or indeed a portion of the posterior arc of a vertebra. FIG. 7 depicts a face view where reference AT identifies the transverse process.

In the above description, both of the portions 42 and 44 of the ligature 14 are disposed in the recesses 30 and 32 on the same side of the rod 18. In some embodiments, the portions 42 and 44 of the ligature 14 may be placed on opposite sides of the rod 18. Under such circumstances, it should be considered that the outside face 18a of the rod 18 and the inside walls of the recesses 30 and 32 define two passageways, respectively for passing each of the portions 42 and 44 of the ligature 14.

FIGS. 8 to 13B depict various view of one embodiment of the fixing system. In these figures, there can be seen the rod 18, the connecting part 12, and the flexible ligature 14.

In this embodiment, the connecting part 12 is constituted by a part 55 that is generally U-shaped. The inside wall of this part 55 is constituted by a bottom 57 of substantially semicylindrical shape and by two substantially plane portions 53 and 54 that correspond to the two limbs of the part 55. The width of the recess 58 formed in the part 55 is substantially equal to the diameter of the rod 18. On its outside face 59 which is circularly symmetrical about a longitudinal axis of the part 55, there is provided a thread 60 occupying its upper portion. The thread 60 is located entirely above the rod 18 when it is put into place in the recess 58. The thread 60 is designed to co-operate with a clamping ring 62 that constitutes the adjustable locking means. This ring has a slightly frustoconical bore 64 with an inside face 66 that carries tapping 68.

In some embodiments, when the ring 62 is screwed tight on the threaded portion 60 of the part 55, it deforms the limbs of the part 55 elastically, thereby pinching and clamping strands of the ligature 14 between the rod 18 and the inside wall(s) of the recess 58, in a manner explained below.

Figure 10:
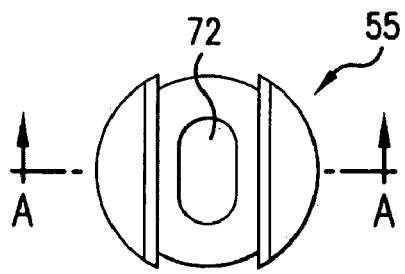
FIG. 10 is a plan view of a portion of the FIG. 9 connection device.
Figure 11:
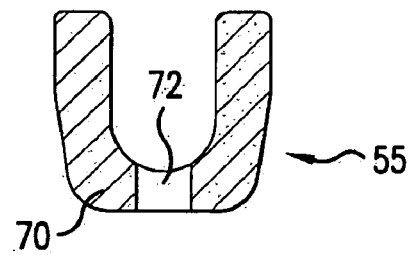
FIG. 11 is a section view on line AA of FIG. 10.

As shown in FIGS. 10 and 11, the part 55 includes in its bottom 70 a passage 72 for passing the ligature 14 in a manner explained below.

Figure 12:
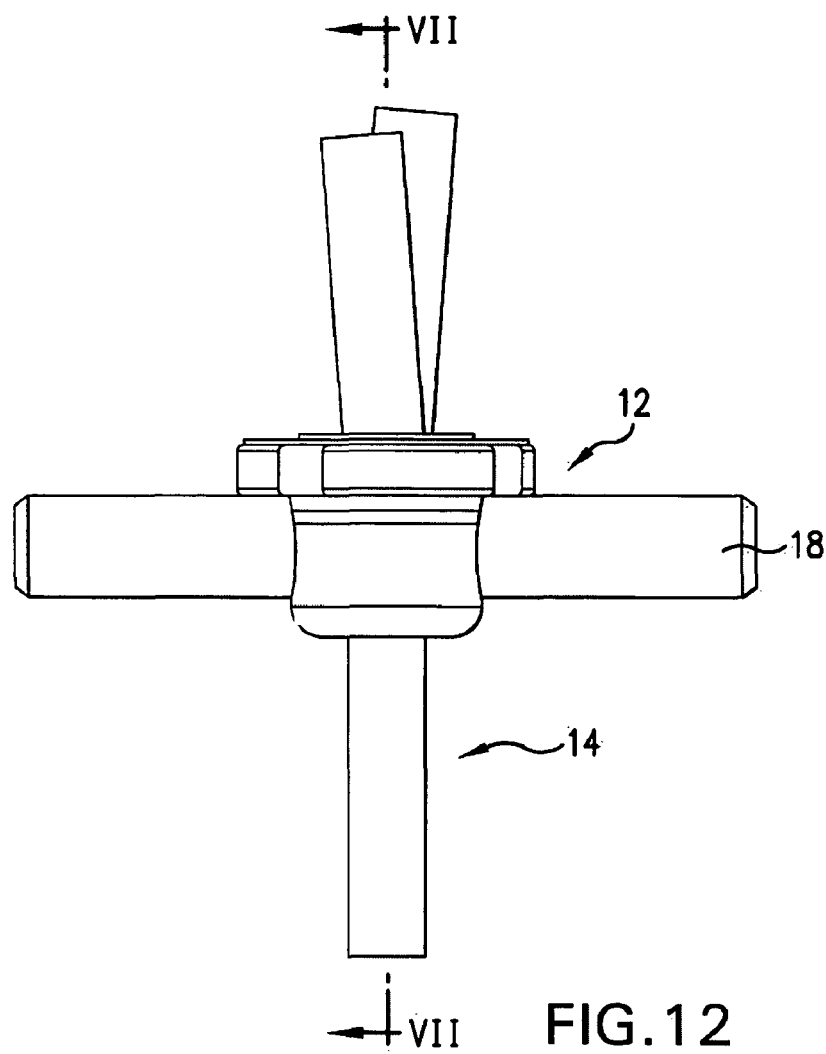
FIG. 12 is a face view of the fixing system of the second embodiment.
Figure 13A:
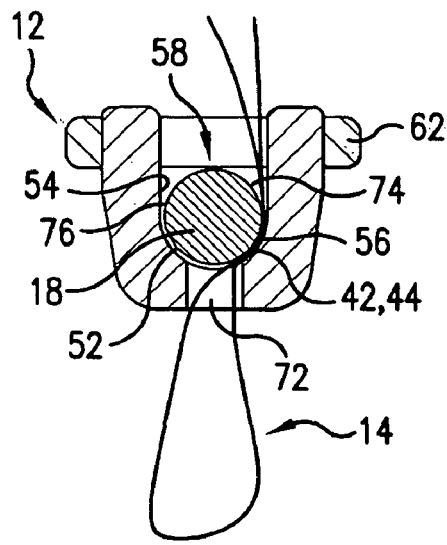
FIGS. 13A and 13B are section views on line VII-VII of FIG. 12 showing two ways in which the flexible ligature can be put into place.
Figure 13B:
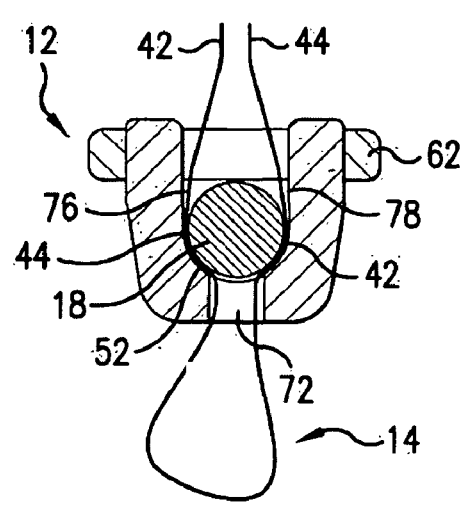

With references to FIGS. 12, 13A, and 13B, there follows a description of two different ways of putting the flexible ligature 14 into place inside the connecting part 12 in the second embodiment. The side wall of the rod 18 and the inside wall of the recess 58 of the part 55 potentially define two passageways 74 and 76 for passing the middle strands of the flexible ligature 14. In the configuration shown in FIG. 13A, only the passageway 74 is used. Thus, both intermediate portions 42 and 44 of the flexible ligature 14 are disposed in the passage 74.

In the configuration shown in FIG. 13B, the middle portions 42 and 44 of the flexible ligature 14 are disposed respectively one in each of the passageways 74 and 76, i.e. on either side of the rod 18. Advantageously, the free ends of the ligature 14 are accessible for exerting the desired traction in order to obtain suitable clamping on the spinous process prior to locking the clamping ring 62 on the part 55.

One advantage to this type of embodiment may be the ability to avoid making two longitudinal parts constituting a kind of clamp hinged on the pin 24. In some embodiments, the locking means are constituted by an element that is distinct from the connecting part and that is removable therefrom. In some embodiments, the locking means co-operate with the connecting part by screw engagement. It is thus possible to adjust accurately the dimensions of the ligature-passing passageway(s) as defined by the connecting part and the rod. In an initial stage, the coefficient of friction between the coefficient of the ligature and secondly the rod and the connecting part can be adjusted. In the final stage, very effective clamping of the ligature is obtained between the rod and the locking part.

In some embodiments, including for example the embodiments shown in FIGS. 14-39, rod 18 may not be needed in order for the bone fixing system to effectively hold a bone in a relative position. The embodiments of the bone fixing system 100 shown in FIGS. 14-39 can include conformable ligature 14 and blocking body 120, which may include compression member 140. In these embodiments that do not require the use of rod 18, the conformable ligature 14 may be passed around one or more bones, tendons, muscles, rods, plates, screws, or other structures in a body and passed through loop passage 126 in blocking body 120 to form a loop extending from a first portion of blocking body 120 and a first end and a second end of conformable ligature 14 may be passed out one or more exit passages 128 in blocking body 120 to extend in a free configuration from a second portion of blocking body 120. Thus, although conformable ligature 14 may, in some uses, pass around rod 18 to capture rod 18 in a loop portion, rod 18 is not necessary for bone fixing system 100 to hold a bone in a secure position.

With reference to FIGS. 14-38, in embodiments that do not require the use of rod 18 to hold a structure in a relative position, bone fixing system 100 may include compression member 140 having a first surface 146 for contact with conformable ligature 14 and for cooperating with inside surface 125 of blocking body 120 to form a passageway for one or more ends of conformable ligature 14. Compression member 140 may be inserted into blocking body 120 before conformable ligature 14 is passed through blocking body 120. In some embodiments, closure member 130 may engage with engagement portion 123 of blocking body 120 before inserting compression member 140 and/or passing conformable ligature 14 through blocking body 120.

In other embodiments that do not require the use of rod 18 to hold a structure in a relative position, bone fixing system 100 may include closure member 130 for engagement with engagement portion 123 of blocking body 120 and for contact with compression member 140 so that advancing closure member 130 into blocking body 120 biases compression member 140 onto conformable ligature 14. Closure member 130 may be advanced into blocking body 120 for biasing compression member 140 against conformable ligature 14 to create a friction force between conformable ligature 14 and blocking body 120. A friction force between conformable ligature 14 and blocking body 120 may hold conformable ligature 14 in place without significant movement relative to blocking body 120. In some embodiments, closure member 130 may be advanced into blocking body 120 for impinging conformable ligature 14 between compression member 140 and blocking body 120 to prevent any relative movement.

Advantageously, the use of compression member 140 in these embodiments enable bone fixing system 100 to be used in circumstances in which rod 18 may be undesirable or unnecessary. Another advantage of the embodiments illustrate in FIGS. 14-38 is the ability for the surgeon to more easily see conformable ligature 14 as it is passed through various passages in the bone fixing system. Another advantage to this embodiment is the reduced size of blocking body 120 over prior art devices that couple to a rod. In particular, the use of compression member 140, particularly having a hemispherical profile, can reduce the height and overall profile of blocking body 120.

Figure 14:
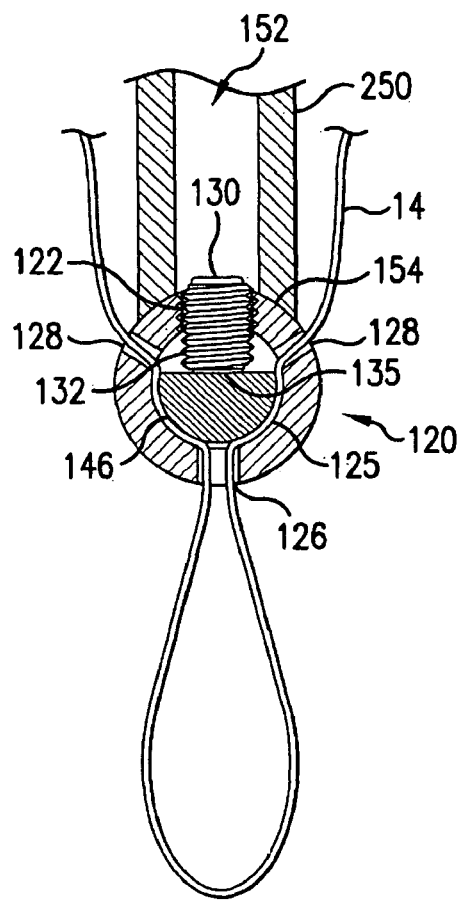
FIG. 14 depicts a cross-sectional end view of one embodiment of a bone fixing system.

FIG. 14 depicts a cross-sectional view of a portion of one embodiment of bone fixing system 100 useful for holding a bone in a position without requiring rod 18. Bone fixing system 100 of FIG. 14 includes blocking body 120 with compression member 140 and closure member 130, ligature 14, and tensioning tool 250. Blocking body 120 of FIG. 14 includes closure member passage 123 for receiving closure member 130 and loop passage 126 and exit passages 128 for receiving ligature 14 through blocking body 120 (e.g., as shown). As shown in FIG. 14, ligature 14 has been passed through blocking body 120 such that each end 14 of ligature 14 extends out of one of exit passage 128 and ligature 14 passes through loop passage 126 to form ligature loop portion 14. In some embodiments, ligature 14 may have a round profile, which can often provide the highest strength per unit of cross-sectional area of ligature 14, enable passing ligature through small openings, and/or reduce the area of contact with a structure. As shown in FIG. 14, ligature 14 may have a wide, flat (or approximately flat) profile which may distribute forces over a larger area, provide higher strength, and/or prevent rolling (e.g. as compare to a round profile). Compression member 140 includes first surface 146 for cooperating with inner surface 125 of blocking body 120 to form a passageway between loop passage 126 and exit passages 128. As shown in FIG. 14, closure member 130 includes threads 132 for engaging threads 122 in engagement portion 123 of blocking body 120 and bottom surface 135 for contact with compression member 140. As shown in FIG. 14, closure member 130 has been engaged with threads 122 in blocking body 120 and bottom surface 135 contacts compression member 140 such that ligature 14 is held in place relative to blocking body 120 due to compression in the passageways formed by first surface 146 and inner surface 125 between loop passage 126 and exit passages 128. As shown in FIG. 14, bone fixing system 100 includes tensioning tool 250 having central passage 152 for passage of ends 14 of ligature 14 and distal end 154 for contact with blocking body 120.

As shown in FIG. 14 (and FIG. 15), blocking body 120 may be manufactured with inner surface 125 for cooperating with first surface 146 of compression member 140 to form a space through which conformable ligature 14 passes and for contacting with a portion of conformable ligature 14 to hold conformable ligature 14 in position. In some embodiments, inner surface 125 may be manufactured with a grooved, knurled, or otherwise textured surface to aid in holding conformable ligature 14 in place. Inner surface 125 of blocking body 120 may be coated, layered, or otherwise treated to aid in holding conformable ligature 14 in place. In some embodiments, inner surface 125 may allow one-way passage of conformable ligature 14 through blocking body 120, for example, by manufacturing inner surface 125 with an asymmetric saw-tooth profile to allow passage of conformable ligature 14 through blocking body 120 in a first direction but to resist movement in the opposite direction.

As shown in FIG. 14, loop passage 126 is located along the arclength opposite (i.e., facing) first surface 146 of compression member 140 positioned in blocking body 120, but it should be understood that loop passage 126 could be positioned at other places around blocking body 120. As shown in the embodiment of FIG. 14, exit passages 128 are located on opposing portions of blocking body 120 and each is located higher than the uppermost portion of compression member 140 when positioned in blocking body 120. However it should be understood that exit passages 128 can be located at other positions around blocking body 120. In various embodiments, loop passage 126 and exit passages 128 may be circular, oval, elliptical, or other shape, may be symmetric or asymmetric, and may be oriented such that conformable ligature 14 may enter or exit blocking body 120 at an angle, normal, or substantially tangential to a portion of blocking body 120. In alternative embodiments, there may only be a single exit passage 128 through which both ends 14 of ligature 14 pass.

As shown in FIG. 14, tensioning tool 250 (discussed in further detail below) has distal end 154 for detachable engagement with a portion of blocking body 120. In some embodiments, distal end 154 of longitudinal member 260 may have passage 152 for accessing closure member 130. As shown in FIG. 14, distal end 154 may be curved for engagement with a portion of blocking body 120 having a generally curved profile.

In some uses, ligature 14 may have one or both ends passed around a structure in the body. Both ends of ligature 14 may be inserted in loop passage 126 to form a loop around the structures. Compression member 140 may be inserted in compression member opening 124. Ligature 14 may be passed through the passageway formed between first surface 146 of compression member 140 and inner surface 125 of blocking body 120. Ends of ligature 14 may be passed out one or more exit passages 128. Closure member 130 may be inserted in engagement portion 123 to engage threads 122. Ends of ligature 14 may be connected to tensioning tool 250, such as tensioning tool 250 shown in FIG. 39. Ligature 14 may be tightened, and closure member 130 may be inserted in engagement portion 123 and advanced until closure member 130 contacts compression member 140. Advancing compression member 140 creates a friction force between ligature 14 and blocking body 120. The friction force may be great enough to impinge ligature 14 relative to blocking body 120 or may be enough to resist movement of ligature 14 relative to blocking body 120.

Figure 15:
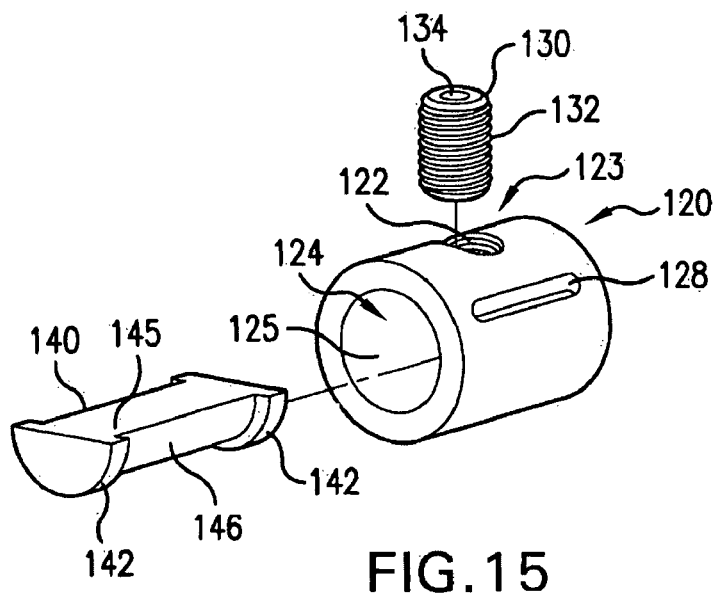
FIG. 15 depicts an exploded perspective view of one embodiment of a blocking body.

FIG. 15 depicts an exploded perspective view of the embodiment of blocking body 120 shown in FIG. 14, including compression member 140 and closure member 130. As shown in FIG. 15, blocking body 120 includes engagement portion 123 having threads 122 for receiving closure member 130, and compression member opening 124 through which compression member 140 may be inserted to "side-load" compression member 140 within blocking body 120. As shown in the embodiment of FIG. 15, closure member 130 includes tool portion 134 and thread 132 and compression member 140 includes first surface 146, second surface 145, and flanges 142.

As shown in FIG. 15, blocking body 120 can include compression member openings 124 on either side of blocking body 120 for insertion of compression member 140. In the embodiment of FIG. 15, compression member opening 124 has a constant diameter, while in alternative embodiments opening 124 may have a first diameter large enough to accommodate flanges 142 and a second diameter smaller than flange 142 but large enough to seat compression member 140. Compression member 140 can be inserted, positioned, and/or removed from blocking body 120. In various embodiments, compression member 140 may be short enough to fit inside blocking body 120, compression member 140 may be substantially the same length as blocking body 120, or compression member 140 may extend some distance beyond blocking body 120. Advantageously, compression member 140 enables embodiments of the bone fixing system 100 to operate in areas of the body or in situations in which a rod may be difficult or undesirable. An advantage to blocking body 120 having compression member opening 124 oriented for side-loading compression member 140 is the ability to adjust the positioning of compression member 140 after closure member 130 has engaged engagement portion 122.

Extensions 142 (such as flanges 142) of compression member 140 can operate to prevent compression member 140 from shifting or moving out of position once closure member 130 has engaged engagement portion 123 of blocking body 120. In operation, closure member 130 will contact compression member 140 to hold ligature 14 substantially in place when ligature 14 has been positioned to hold a bone or other structure in a relative position. In some embodiments, extensions 142 may extend around the entire arclength of first surface 146 of compression member 140, such as flanges 142 depicted in FIG. 15, while in other embodiments, extensions 142 may extend around a portion of the arclength of first surface 146. In some embodiments, a radius of extension 142 may allow insertion or removal of compression member 140 in a first orientation and may prevent removal or insertion in a second orientation. For example, in some embodiments, extensions 142 may have a radius to enable compression member 140 to be inserted into blocking body 120 when compression member 140 is rotated to a first angle, while preventing compression member 140 from being removed when compression member 140 is rotated (e.g., 90 degrees) from the first angle. In some embodiments, compression member 140 may have a variable radius.

As shown in the embodiment of FIG. 15, first surface 146 of compression member 140 can form a passageway in cooperation with inner surface 125 of blocking body 120 for passing ligature 14 and for contacting conformable ligature 14. In some embodiments, first surface 146 may be knurled, grooved, or otherwise machined, may be coated, layered, or otherwise treated for contact with conformable ligature 14, and/or may allow one-way passage of conformable ligature 14 through compression member 140 (e.g., having an asymmetric saw-tooth profile for allowing passage of conformable ligature 14 past compression member 140 in a first direction but resisting passage in an opposite direction).

Various mechanisms can be used to allow closure member 130 to engage engagement portion 123 of blocking body 120. In some embodiments, closure member 130 has helically wound thread 132 and can be advanced in blocking body 120 through engagement passage 123 by rotating closure member 130 to engage threads of engagement portion 123 of blocking body 120. In some embodiments, tool portion 134 on closure member 130 can be a hex shaped receiving are that would allow a surgeon to use a hex tool to engage and rotate closure member 130 so that threads 132 engage with the threads of engagement portion 123. In some embodiments, closure member 130 may have a sawtooth profile or other profile for ratcheting closure member 130 into blocking body 120. Those of ordinary skill in the art will recognize a variety of other mechanisms (some of which will be described herein) for engaging closure member 130 with engagement portion 123 in order to enable closure member 130 to contact compression member 140 and secure in place ligature 14.

Advantages to embodiments of bone fixing systems 100 such as the one depicted in FIGS. 14 and 15 include the curved profile of blocking body 120, which can result in an overall lower profile and/or in less stress on surrounding tissue based on friction contact.

Figure 16:
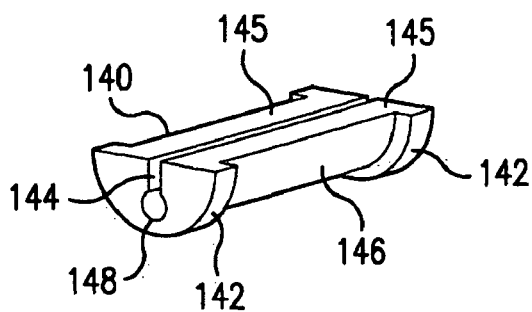
FIG. 16 depicts a perspective view of one embodiment of a compression member.

FIG. 16 depicts a perspective view of an alternative embodiment of compression member 140 of FIGS. 14 and 15 having longitudinal slot 144 and stress reducer 148. In some embodiments, compression member 140 may have a length and width such that when compression member 140 is positioned inside blocking body 120, first surface 146 is in contact with inner surface 125 of blocking body 120 (or first surface 146 is in contact with conformable ligature 14 which is in contact with inner surface 125 of blocking body 120, for example as shown in FIG. 14). In various embodiments, compressing on second surface 145 may bias first surface 146 against inner surface 125 and the radius of curvature of first surface 146 may effectively change some amount, based at least in part on the length and depth of longitudinal slot 144. One advantage to compression member 140 having longitudinal slot 144 is the capability to adjust the compressive force exerted by compression member 140 on ligature 14. In addition to the length and depth of longitudinal slot 144, the amount that the radius of curvature can change can depend on the compression force applied to second surface 147, the shape of inner surface 125, the deformability of any coating, layer, a machined feature of inner surface 125 or first surface 146, the thickness of conformable ligature 14, or the original shape of first surface 146. As shown in the embodiment of FIG. 16, longitudinal slot 144 can include stress reducer 148, which can advantageously prevent or reduce the likelihood of compression member 140 cracking or other material failure due to a change in curvature of first surface 146. While other shapes can be employed, stress reducer 148 may be generally circular or other non-angular shape to prevent the build-up of stresses associated with bending forces. The radius and position of stress reducer 148 may be based on the material used for compression member 140, the radius of curvature of first surface 146, the depth and width of longitudinal slot 144, the anticipated compression force applied to second surface 147, or the length of compression member 140.

Figure 17:
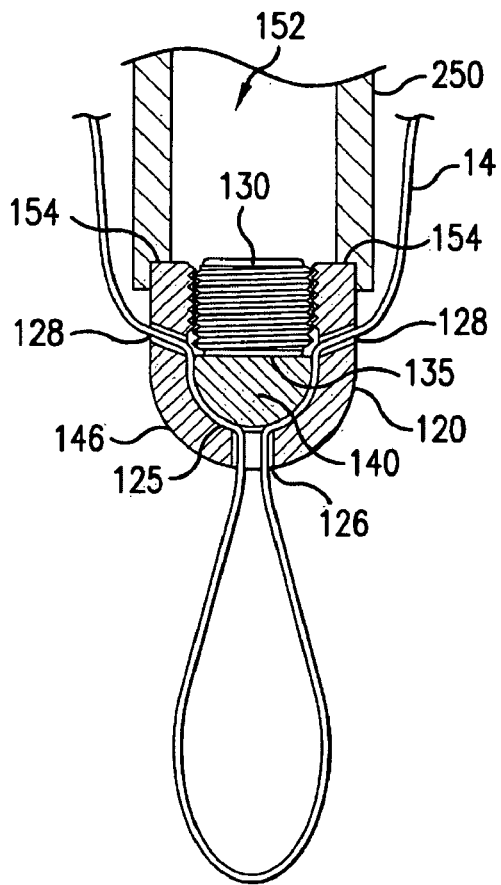
FIG. 17 depicts a cross-sectional end view of one embodiment of a bone fixing system.
Figure 18:
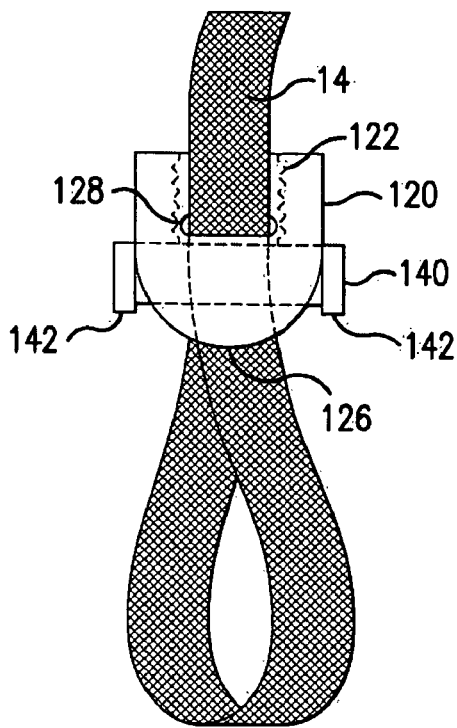
FIG. 18 depicts a side view of one embodiment of a bone fixing system.
Figure 19:
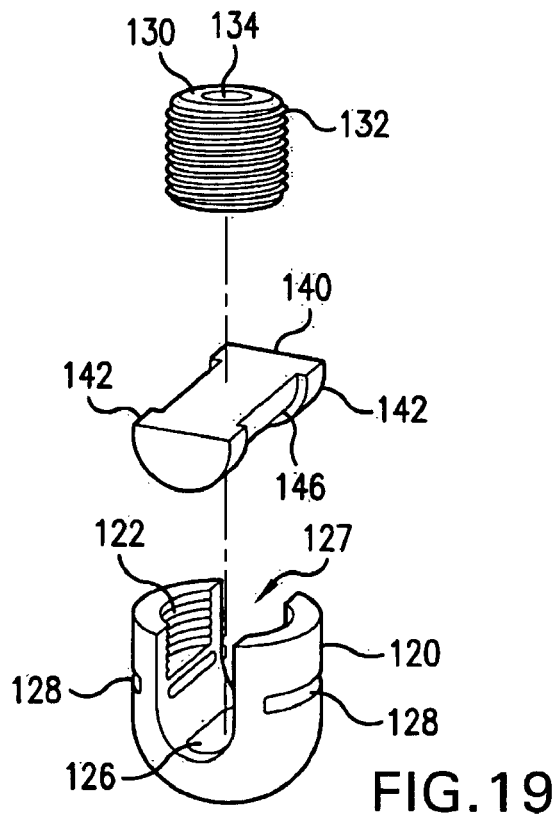
FIG. 19 depicts an exploded view of one embodiment of a blocking body.

FIGS. 17-19 illustrate another embodiment of the bone fixing system 100. FIG. 19 is a perspective view of this embodiment of blocking body 120, in which compression member 140 and closure member 130 may be top-loaded or side-loaded into blocking body 120 via U-shaped channel 127. In this embodiment, blocking body 120 is shown to include two upwardly extending walls forming a generally U-shaped channel 127. Compression member 140 is shown with a similar "dual cylinder" shape as the compression member 140 of FIG. 16 (in fact, the compression member of FIG. 16 can be used in the FIG. 17 embodiment) with first surface 146 and flanges 142. As shown in FIG. 18, compression member 140 may extend some distance beyond blocking body 120 with extensions 142 on compression member 140 designed to prevent compression member 140 from moving laterally once compression member 140 is positioned in blocking body 120. As shown in the FIG. 18 embodiment, extensions 142 may be located exterior to blocking body 120 (while in alternative embodiments, extensions 142 may be located interior to blocking body 120).

Compression member 140 can be placed within channel 127 with surface 146 contacting inner wall 125 at the bottom of channel 127. Closure member 130 may be inserted into channel 127 (e.g., by engaging the exterior threads on the body of closure member 130 with the interior threads of channel 127) for engaging engagement portion 122. Advancing closure member 130 down channel 127 (e.g., rotating closure member 130) can force compression member 140 against ligature 14 to hold ligature 14 in place without significant movement (or with complete impingement) relative to blocking body 120.

FIG. 17 shows a cross-sectional view of this embodiment of bone fixing system 100 using the blocking body 120 of FIG. 19 in which compression member 140 is either side or top-loaded into blocking body 120. As shown in FIG. 17, conformable ligature 14 may be passed through loop passage 126 in blocking body 120 to form a loop extending from blocking body 120 and first and second ends may be passed out one or more exit passages 128 to extend from a second portion of blocking body 120. In order to use the bone fixing system 100 to hold a bone in position, compression member 140 may be inserted in blocking body 120 after conformable ligature 14 has been passed through blocking body 120. Closure member 130 may be engaged to engagement portion 122 of blocking body 120 after conformable ligature 14 has been passed through blocking body 120 and after compression member 140 has been positioned in blocking body 120.

Engaging closure member 130 in engagement portion 122 of blocking body 120 prevents all or significant movement of conformable ligature 14 relative to blocking body 120.

As shown in FIG. 17, exit passages 128 can be positioned higher than first surface 146 of compression member 140 in order to provide a longer passage between first surface 146 of compression member 140 and inner surface 125 of blocking body 120 to provide a higher friction coefficient or reduced point stresses on conformable ligature 14, blocking body 120, and/or compression member 140. In alternative embodiments, exit passages 128 may be positioned near engagement portion 122 such that closure member 130 may contact conformable ligature 14. In various embodiments, closure member 130 may impinge a portion of conformable ligature 14. As shown in FIG. 17, exit passages 128 may be located on blocking body 120 such that when distal end 154 of tensioning tool 250 engages blocking body 120, first and second ends of ligature 14 are external of distal end 154. However, it should be understood that exit passages 128 may be located at a number of locations on the blocking body 120 and relative to tensioning tool 250. Distal end 154 of tensioning tool 250 may engage a portion of blocking body 120 to enable a surgeon to tension conformable ligature 14 in order to hold a bone or structure in position. In various embodiments, distal end 154 of tensioning tool 250 may be flanged for engaging blocking body 120. Tensioning tool 250 may include passage 152 along the entire length of tensioning tool 250 for accessing closure member 130 or passage 152 may extend a selected length of tensioning tool 250.

FIG. 18 depicts a side view of this embodiment of bone fixing system 100 where conformable ligature 14 passes through loop passage 126 to form a loop extending from a first portion of blocking body 120, and further passes through a passage formed by compression member 140 and blocking body 120, and passes out both exit passages 128 (though ligature 14 could in various embodiments pass both ends through a single exit passage 128). FIG. 18 illustrates the flanges 142 extending outside of blocking body 120.

As described, closure member 130 may be top-loaded into blocking body 120 for the embodiments of FIGS. 17-19. One advantage to top-loading closure member 130 and compression member 140 is that closure member 130 may be integrated with compression member 140 to form a unitary piece, which reduces the number of components that the surgeon has to implant during surgery. In various embodiments, closure member 130 may be connected to compression member 140 by a pin (not shown) to form a unitary piece. In some embodiments, closure member 130 may rotate while compression member 140 does not rotate. One advantage to this unitary closure member/compression member embodiment is that compression member 140 may apply only compression forces to ligature 14. In contrast, if compression member 140 rotates inside blocking body 120, torsion may be applied to ligature 14.

Figure 20:
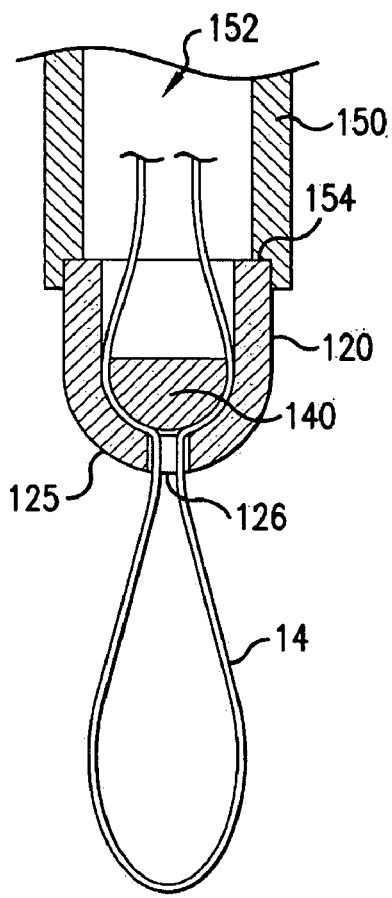
FIG. 20 depicts an exploded view of one embodiment of a bone fixing system.
Figure 21:
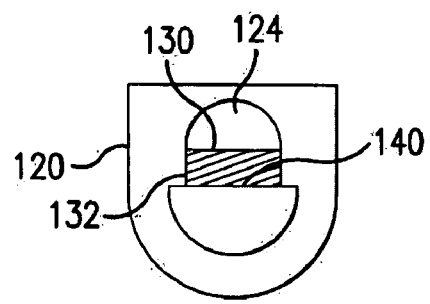
FIG. 21 depicts a side view of one embodiment of a blocking body.
Figure 22:
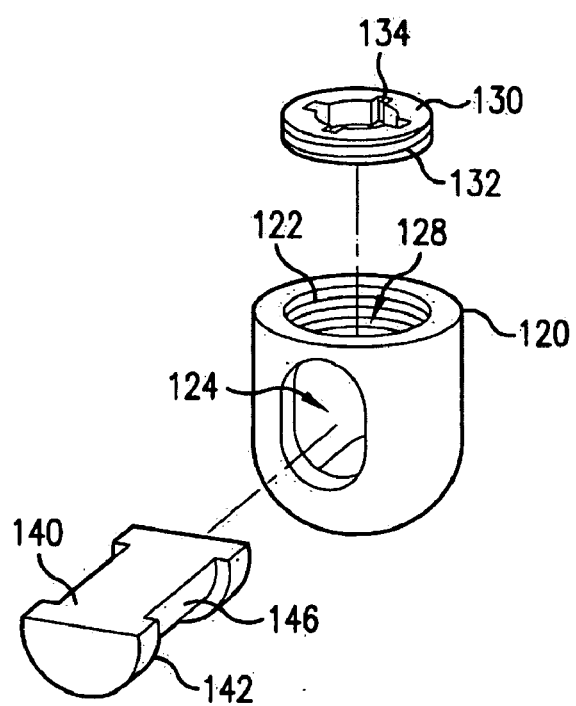
FIG. 22 depicts an exploded view of a portion of a blocking body.

FIGS. 20-22 depict yet another embodiment of bone fixing system 100 in which conformable ligature may be passed around one or more bones, tendons, muscles, rods, plates, screws, or other structures in the body, and then passed through loop passage 126 in blocking body 120 to form a loop extending from a first portion of blocking body 120. Ligature 14 can then be passed through a passageway formed by first surface 146 of compression member 140 and inner surface 125 of blocking body 120, and passed out through the center of blocking body 120 to extend out of blocking body 120 so that ends 14 of ligature 14 can be in a free configuration. Tensioning tool 250 may have a central passage 152 to allow first end and second end of ligature 14 to pass through.

FIG. 21 depicts a side view of a portion of one embodiment of blocking body 120, in which compression member 140 may be side-loaded through compression member opening 124 into blocking body 120. As shown, blocking body 120 of FIG. 21 has a similar shape to the blocking body 120 of FIG. 19, except that the FIG. 21 embodiment of blocking body 120 encloses compression member 140 (as opposed to the "open" top of the blocking body 120 of FIG. 19). Thus, in the FIG. 21 embodiment, compression member 140 may be pre-loaded into blocking body 120 or even manufactured to be permanently enclosed within blocking body 120. In an alternative embodiment, compression member 140 and/or extensions 142 may be manufactured with dimensions such that once compression member 140 is inserted in blocking body 120, the position of compression member 140 may be altered but compression member 140 may not be removed from blocking body 120. In other words, in the embodiment shown in FIG. 21, compression member 140 may be moved around inside blocking body 120, but may not be removed. In various embodiments, blocking body 120 may be manufactured with compression member opening 124 having a first set of dimensions and after compression member 140 is inserted into blocking body 120 through opening 124, the size of opening 124 may be altered (e.g., by adding material or altering the shape of blocking body 120 at opening 124) to reduce opening 124 dimension to prevent removal of compression member 140. Alternatively, compression member 140 may be manufactured having a first set of dimensions, inserted into opening 124 of blocking body 120, and then altered, such as by adding material, to increase the dimensions of compression member 140 to prevent removal of compression member 140. In various embodiments, compression member 140 may be compression fit or sweat-locked through opening 124 into blocking body 120. In another embodiment, blocking body 120 may be manufactured with two upwardly extending walls, compression member 140 may be inserted in a channel formed by the two walls, and material may be added to convert the channel into opening 124.

FIG. 22 depicts an exploded perspective view of the embodiment of blocking body 120 of FIGS. 20 and 21 in which compression member 140 may be side-loaded into blocking body 120 and closure member 130 may threadably engage engagement portion 122 of blocking body 120. A tool may engage with tool portion 134 for rotating closure member 130 to engage external threads 132 on closure member 130 with internal threads 122 in blocking body 120. Tool portion 134 of closure 130 can be hollow to enable one or more ends of conformable ligature 14 to pass through and extend out exit passage 128.

Figure 23:
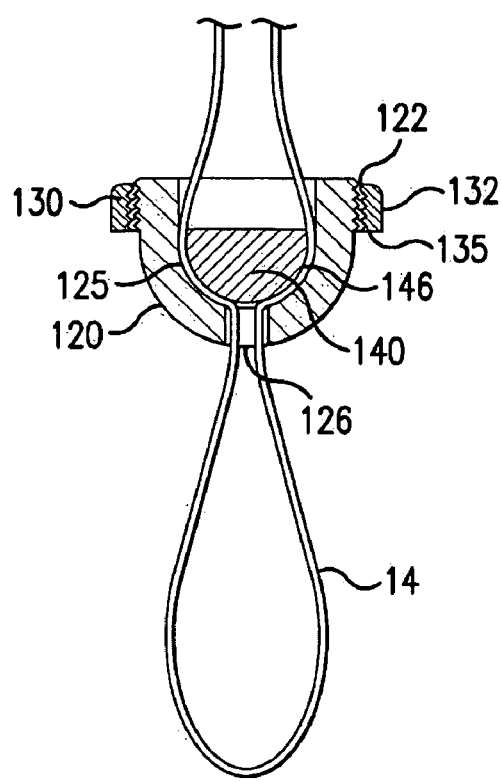
FIG. 23 depicts a cross-sectional end view of one embodiment of a bone fixing system.
Figure 24:
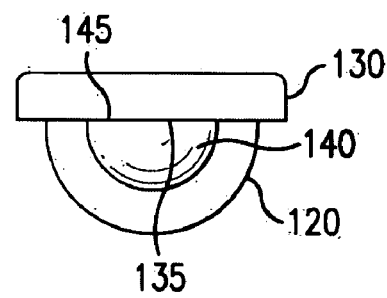
FIG. 24 depicts a side view of one embodiment of a blocking body.
Figure 25:
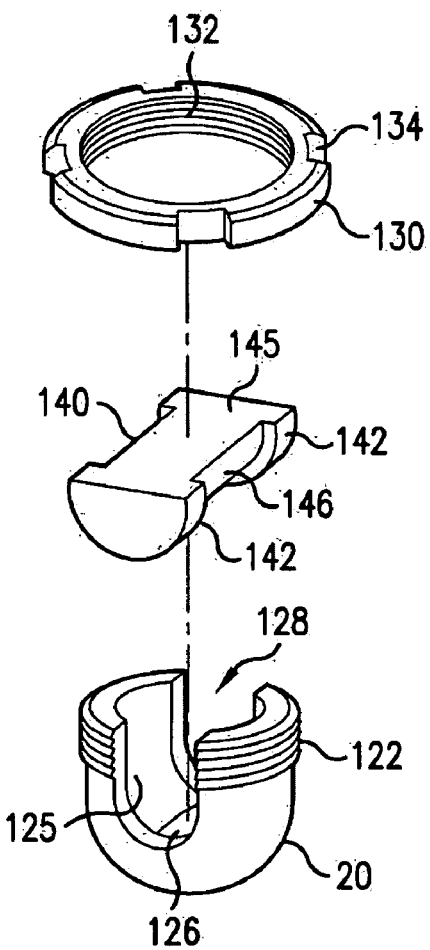
FIG. 25 depicts an exploded view of one embodiment of a blocking body.

FIGS. 23-25 show another embodiment of a bone fixing system 100 having an alternate closure mechanism and exit passage. FIG. 23 depicts a cross sectional end view of bone fixing system 100 in which conformable ligature 14 may be passed through loop passage 126 in blocking body 120 to form a loop extending from a first portion of blocking body 120, through a passage formed by first surface 146 of compression member 140 and inner surface 125 of blocking body 120, and extend out through exit passage 128. As shown in FIGS. 23 and 25, in this embodiment, ring-style closure member 130 may have internal threads 132 for engaging external threads 122 on blocking body 120. This type of embodiment will provide the advantage of allowing the surgeon to see conformable ligature 14 as it passes through loop passage 126 in blocking body 120 and to see compression member 140 as it is positioned in blocking body 120.

FIG. 24 depicts a side view of the FIG. 23 embodiment in which bottom surface 135 of closure member 130 is in contact with second surface 145 of compression member external to blocking body 120, and in this embodiment bottom surface 135 of closure member 130 contacts second surface 145 at extensions 142 of compression member 140. An advantage to this type of embodiment is the ability for the surgeon to see the engagement between threads 132 on closure member 130 with threads 122 on blocking body 120. As shown in FIG. 24, tool portions 134 of closure member 130 may be positioned on an exterior portion of closure member 130. An advantage to this type of embodiment is the ability for a tool (not shown) to engage tool portions 134 exterior to distal end 154 (not shown) engaged with a portion of blocking body 120. This exterior engagement can provide a superior tightening mechanism to engage closure member 130 with blocking body 120 in certain embodiments.

FIG. 25 depicts an exploded perspective view of the FIG. 24 view with the various portions of blocking body 120 separated prior to engagement of closure member 130 onto blocking body 120. An advantage to this embodiment is the reduced number of passages, which may reduce the time needed to implant the system.

Figure 26:
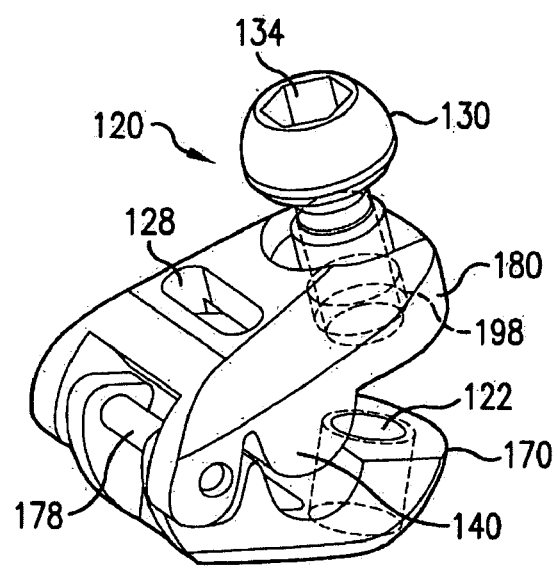
FIG. 26 depicts a perspective view of one embodiment of a blocking body.
Figure 27:
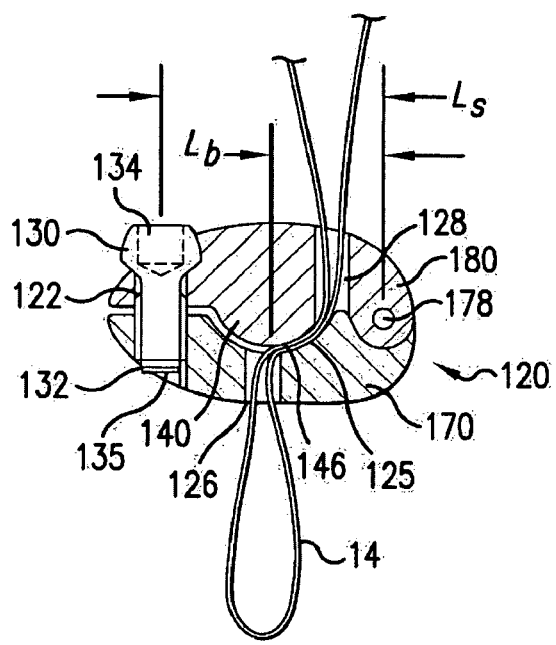
FIG. 27 depicts a cross-sectional side view of one embodiment of a bone fixing system.
Figure 28:
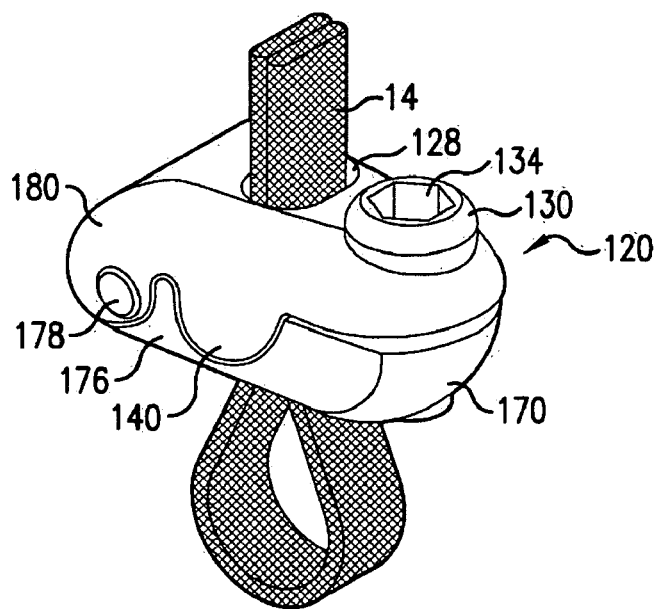
FIG. 28 depicts a perspective view of one embodiment of a bone fixing system.

FIGS. 26-28 illustrate an alternative embodiment of bone fixing system 100 that provides a hinged closing mechanism offset from ligature 14 that also does not require a rod, and which can provide certain advantages over other embodiments. FIG. 26 shows blocking body 120 with first portion 170 hingedly connected via hinge pin 178 to second portion 180. Conformable ligature 14 can pass through loop passage 126 in first portion 180 of blocking body 120 to form a loop extending from first portion 180 of blocking body 120, further passed through a passage formed between first surface 146 of compression member 140 and inner surface 125 of blocking body 120, and then passed through exit passage 128 in second portion 170. As with every embodiment described, ligature 14 may get to this desired configuration (with a loop portion extending from blocking body 120) in a variety of ways. An advantage to this embodiment is the low profile possible due to the configuration of closure member 130 offset from compression member 140.

In various embodiments, hinge pin 178 connects first portion 170 to second portion 180 in either a permanent manner or alternatively the hinged connection may be disconnectable. The hinged connection can be formed so as to allow two-way hinged motion for engaging or disengaging first portion 170 from second portion 180. In an alternative embodiment, the hinged connection may allow one-way hinged motion for engaging first portion 170 from second portion 180 but may subsequently prevent first portion 170 from disengaging second portion 180. In various embodiments, first portion 170 and/or second portion 180 may allow hinged motion between a selected arclength, for example, first portion 170 and second portion 180 may move through an arc of approximately 180 degrees.

As further shown in FIGS. 26-28, closure member 130 will be used to close the hinged bone fixing system 100 in a manner to hold ligature 14 in a relatively or completely stable position relative to blocking body 120. Closure member 130 of FIG. 27 is shown having external threads 132 for engaging internal threads 122 in engagement portion 123 of blocking body 120. Second portion 180 may include engagement portion 122 for engagement by threads 132 on closure member 130. In one embodiment, closure member 130 may be positioned within first portion 170 such that closure member 130 is free to rotate in first portion 170 to join first portion 170 with second portion 180, but may not be removed from first portion 170 after such engagement. In other words, in some embodiments, closure member 130 may be rotated to engage threads on closure member 130 with engagement portion 122 to collapse first portion 170 and second portion 180, and the direction of rotation may be reversed to disengage closure member 130 from engagement portion 122, but closure member 130 may not be removed from first portion 170. In the embodiment shown in FIG. 26, closure member 130 can be rotatably positioned in second portion 180 such that closure member 130 is free to rotate in second portion 180 but may not be removed from second portion 180, which can provide the advantage of reducing the risk of having loose hardware (which can be lost inside a patient during surgery) associated with bone fixing system 100.

FIG. 27 depicts a cross-sectional side view of a portion of the embodiment of bone fixing system 100 depicted in FIG. 26, in which conformable ligature 14 may be passed through loop passage 126 in first portion 170 to form a loop extending from first portion 170 of blocking body 120, passed through a passage formed by first surface 146 of compression member 140 and inner surface 125 of blocking body 120, and extend from exit passage 128 in second portion 180. As shown in FIG. 27, first portion 170 and second portion 180 rotate about hinge pin 178 to open or close blocking body 120. Tool portion 134 on closure member 130 may be rotated so threads 132 on closure member 130 engage threads 122 in engagement portion 123. Once bottom surface 135 of closure member 130 reaches a selected point, first portion 170 and second portion 180 compress to impinge movement of ligature 14 relative to blocking body 120.

First surface 146 of compression member 140 and inner surface 125 of blocking body 120 provide a passageway through blocking body 120. In some embodiments, inner surface 125 may be located on first surface 170 and first surface 146 of compression member 140 may be located on second portion 180 as depicted in FIG. 27. In some embodiments, inner surface 125 may be located on second surface 180 and first surface 146 of compression member 140 may be located on first portion 170.

Closure member 130 may be offset from compression member 140 such that threaded engagement of threads 132 of closure member 130 with engagement portion 122 of blocking body 120 may indirectly apply compression to compression member 130. In other words, compression member 140 may be positioned some distance $L_b$ from hinge pin 178 and closure member 130 may be positioned some distance $L_s$ from hinge pin 178. Compression of compression member 140 onto conformable ligature 14 may not be accomplished by directly contacting bottom surface 135 of closure member 130, but may instead be accomplished by rotatably engaging threads 132 with threads 122 to advance closure member 130 in blocking body 120 such that second portion 180 may be leveraged around the fulcrum created by hinge pin 178. An advantage to one embodiment uses the mechanical advantage of $L_s/L_b$ to apply compression forces on conformable ligature 14. Another advantage to one embodiment is the ability for the surgeon to apply large compression forces to conformable ligature 14 due to the mechanical advantage based on the position of hinge pin 178, compression member 140, and closure member 130. The compression forces available may also be based on the radius of curvature of compression member 140, the size or pitch of threads 132 and 122, and/or the size of hinge pin 178. Another advantage may be the precision in which a friction coefficient may be selected between conformable ligature 14 and blocking body 120. In some embodiments, the pitch, shank diameter, or other dimensions of closure member 130 may enable control of the application of compression. For example, a large number of threads per inch may allow more compression due to the mechanical advantage of threads 122 engaging with threads 132, and the application may be more controlled due to the greater angular rotation needed to advance closure member 130 the same distance as closure members 130 having lower numbers of threads per inch. Another advantage to this embodiment relates to the outer surface of first portion 170 and/or second portion 180. Because blocking body 120 can achieve a mechanical advantage through the use of hinge pin 178, closure member 130 may be made smaller than prior art approaches, which allows blocking body 120 to have a smaller opening 123. As shown in FIG. 27, second portion 180 has an outer surface that is curved, which may reduce pain, discomfort, or other undesirable effects that result from using an angular implant.

FIG. 28 depicts a perspective view of the embodiment of FIGS. 26 and 27 shown in a closed configuration, where ligature 14 is held completely or substantially in place relative to blocking body 120. One advantage to this type of embodiment may be the ability to pass conformable ligature 14 around one or more bones, tendons, muscles, rods, plates, screws, or other structures in the body, pass conformable ligature 14 through blocking body 120 out a single exit passage 128, and engage closure member 130 on blocking body 120, but offset from conformable ligature 14 and/or compression member 140. One advantage may be that tensioning tool 250 may not need passage 152 in distal end 154 because closure member 130 (e.g., tool portions 134) may be accessed outside tensioning tool 250.

It should be understood that the various closure mechanisms, closure members, exit passages, and blocking bodies, and other design features shown in the various embodiments of bone fixing system 100 of FIGS. 14-28 may potentially be used in the other embodiments of FIGS. 14-28. For example, the ring-style closure member 130 of the FIG. 25 embodiment can be used on the embodiment of FIG. 22 by modifying the blocking body of FIG. 22 to have external threads onto which the internal threads of the ring-style closure member 130 would engage.

FIGS. 29-38 depict embodiments of bone fixing system 100 in various configurations, arrangements and orientations. In FIGS. 29-38, the embodiment of blocking body 120 is the embodiment depicted in FIGS. 26-28. However, any of the embodiments depicted in FIGS. 14-28 and variations may be used without departing in scope from the present disclosure.

Figure 29:
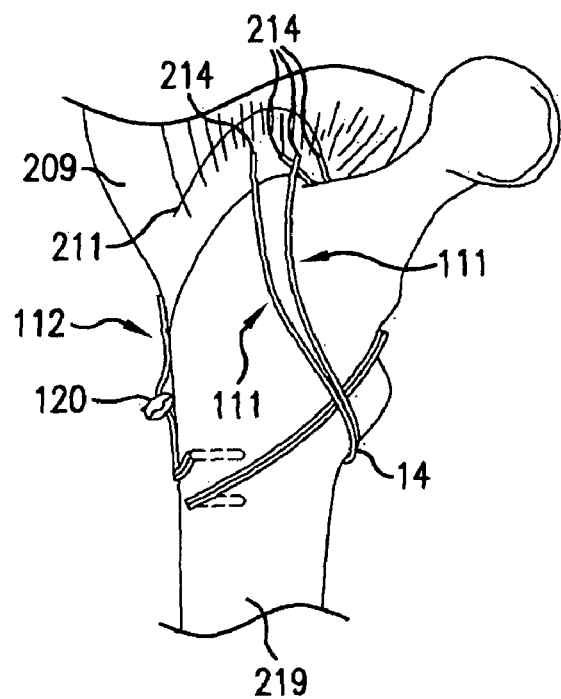
FIG. 29 depicts a perspective view of one embodiment of a bone fixing system attached to a portion of bone.

FIG. 29 depicts a perspective view of one embodiment of bone fixing system 100 for holding a bone in a position. Bone fixing system 100 may be useful for orthopedic applications, such as holding a bone near a tendon or muscle. Portions 214 of conformable ligature 14 may be passed through or around a portion of a muscle and through or around a portion of a femur to provide support while a tear or cut in the muscle heals. Advantageously, blocking body 120 may be positioned at various locations near the muscle, tendon, or bone based on the type or extent of the injury, trauma, or illness, surgical preferences such as MIS access, or patient health such as age or weight, or the like Advantageously, embodiments of bone fixing system 100 may be implanted near other surgical implants without affecting their placement or function. In various embodiments, bone fixing system 100 may include blocking body 120 indirectly applying tension to conformable ligature 14. For example, in the embodiment depicted in FIG. 29, bone fixing system 100 may be implanted to maintain bone 219 in a position with muscle 209 while wound 211 heals. In this embodiment, conformable ligature 14 may be passed around bone 219 and through muscle 209, and through blocking body 120 located on portion 112 of conformable ligature 14 such that substantially all tension between muscle 209 and bone 219 may be supported by portion 111 of conformable ligature 14.

Figure 30:
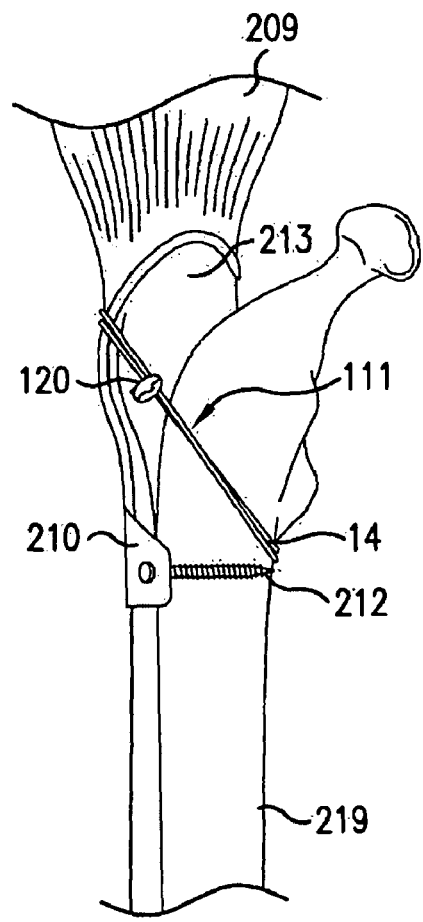
FIG. 30 depicts a posterior view of one embodiment of a bone fixing system attached to a portion of a bone.

Bone fixing systems 100 may be implanted without affecting plates, rods, or other implanted structures. Bone fixing systems may be implanted without affecting bone screws, hooks, bolts, or other implanted hardware. FIG. 30 depicts one embodiment of conformable ligature 14 passed around a part of bone 219, muscle 209 and/or tendon 213 and through blocking body 120, and further depicts bone screw 212 and plate 210 implanted on a portion of bone 219. In this type of embodiment, bone fixing system 100 including blocking body 120 may be positioned on portion 111 of conformable ligature 14 such that some of the tension between muscle 209 and bone 219 may be supported by blocking body 120.

Figure 31:
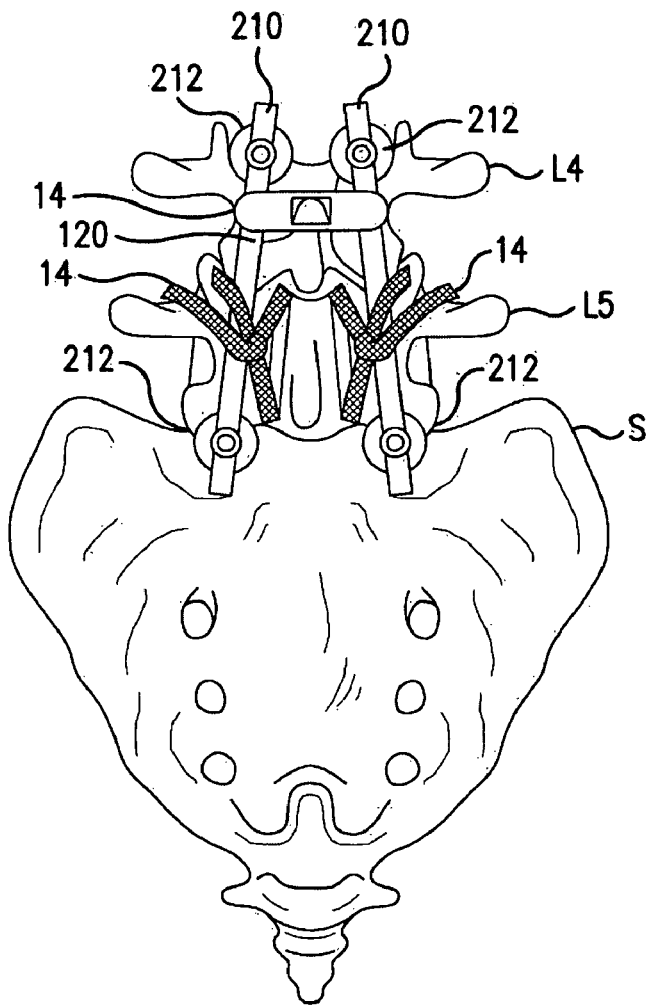
FIG. 31 depicts a sagittal view of one embodiment attached to a portion of a spine, illustrating a method for repairing a spine.
Figure 32:
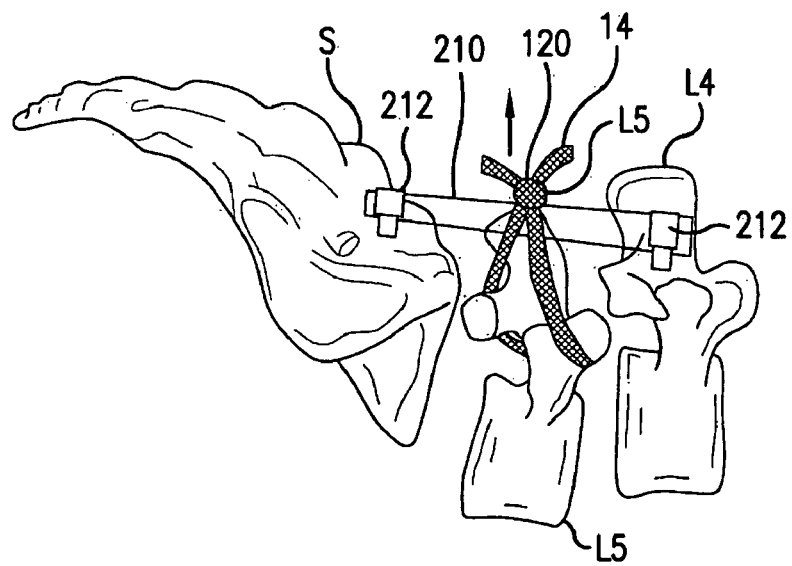
FIGS. 32-38 depict views of a bone fixing system implanted on a spine.

Bone fixing system 100 may be advantageous for correcting alignment of one or more bones. Conformable ligatures 14 and blocking bodies 120 may be useful for correcting alignment of a portion of the spine. FIGS. 31 and 32 depict posterior and sagittal views of a portion of the spine in which bone fixing system 100 may be useful for aligning vertebra L5 with adjacent vertebrae L4 and sacrum S. In some embodiments, bone fastener assemblies 212 may be implanted in lumbar vertebra L4 and sacrum S. In some embodiments, bone fastener assemblies 212 may be inserted through an incision in the skin and implanted using Minimally Invasive Surgery (MIS) techniques, and ligature 14 may be passed around one or more structures.

Figure 33:
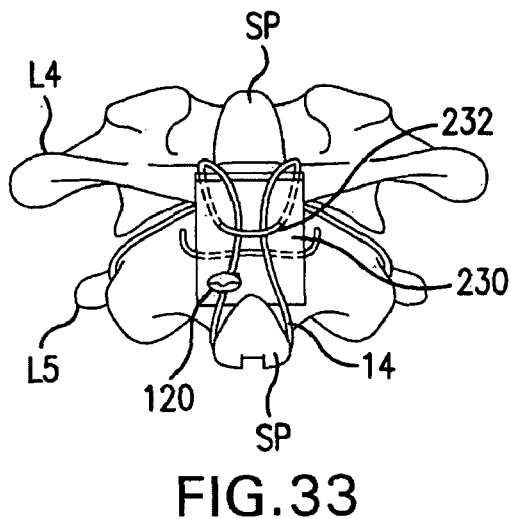

In some embodiments, passing may include going into, through, or out of a structure. In some embodiments, passing may include going over, under, or around a structure. In some embodiments, passing may include crossing over other ligatures 14 or portions of ligatures 14. In some embodiments, passing may include multiple passes along the same path FIGS. 33-38 depict various embodiments of bone fixing systems in place on a portion of a spine. In FIGS. 33-38, bone fixing system 100 is shown holding bone graft 230, which may be useful for supporting a portion of the spine. However, embodiments of bone fixing system 100 may be used to correct problems with the spine without rods, bone grafts, plates, or other implants. Conformable ligature 14 may be passed around a portion of a bone, such as spinous process SP Conformable ligature 14 may be passed around a portion of bone graft 230. Passing conformable ligature 14 around a portion of bone graft 230 may include passing a portion of conformable ligature 14 through a portion of bone graft 230. One end of conformable ligature 14 may be inserted and passed through blocking body 120 from one side and the other end of conformable ligature 14 may be inserted and passed through blocking body 120 from another side, as depicted in FIG. 33.

Figure 34:
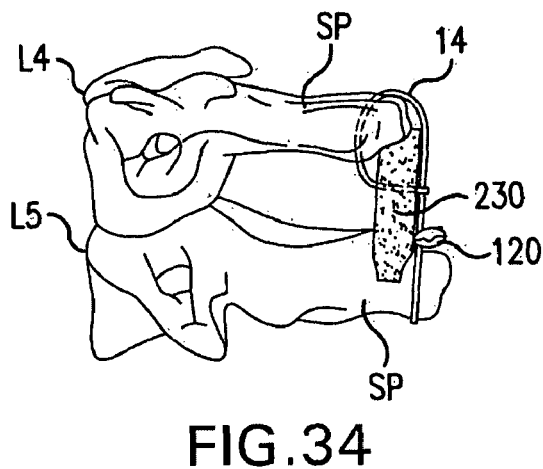
Figure 35:
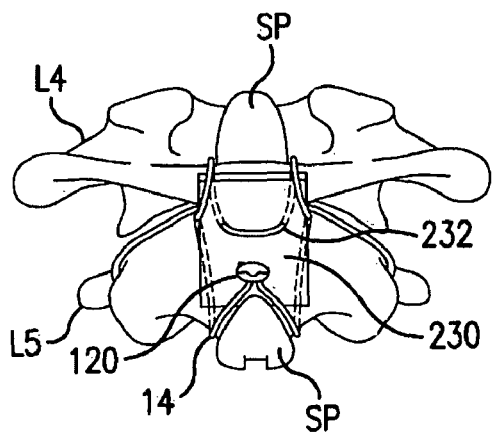
Figure 36:
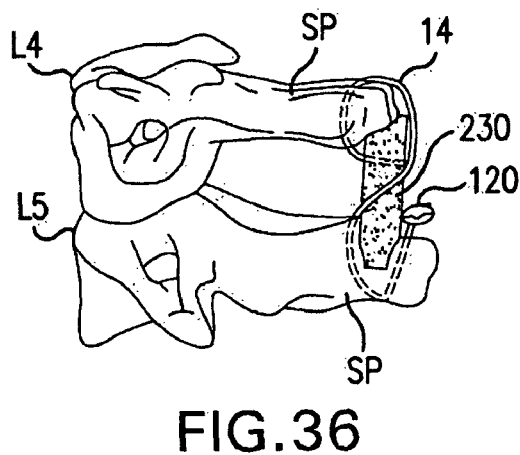
Figure 37:
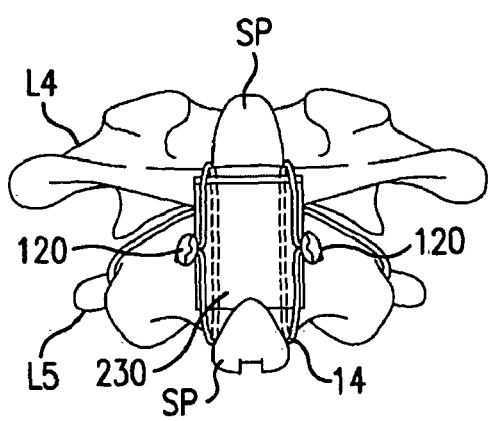
Figure 38:
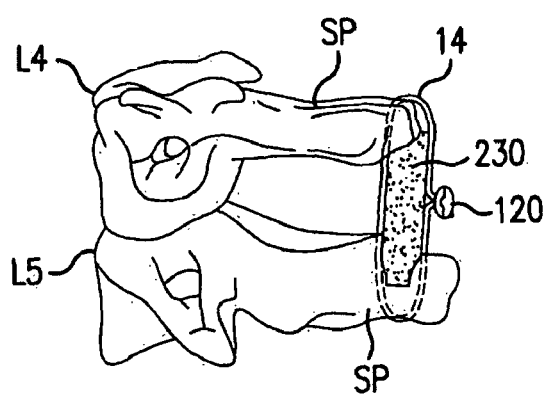

Advantageously, conformable ligature 14 may be selectively passed around structures such as bones and bone grafts. Conformable ligature 14 may be passed around a bone, bone graft, tendon, or other tissue due to disease, injury, tumor, degenerative effects or the like. For example, FIG. 33 depicts a posterior view of one embodiment in which conformable ligature 14 may be passed around a portion of spinous process SP on lower vertebra L5. FIG. 33 further depicts one embodiment in which conformable ligature may be passed through bone, such as the pedicle of lower vertebra L5. As another example, FIG. 34 depicts a sagittal view of one embodiment in which conformable ligature 14 may be passed around the posterior portion of spinous process SP. As another example, FIG. 35 depicts a posterior view of one embodiment in which conformable ligature 14 may be passed around a portion of the pedicle portion of lower vertebra L5. As another example, FIG. 36 depicts a sagittal view of one embodiment in which conformable ligature 14 may be passed around the pedicle portion and the posterior portion of spinous process SP. In some embodiments, ligature 14 may not be passed around a structure FIG. 37 depicts a posterior view of one embodiment in which conformable ligature 14 may be passed around a portion of the pedicle portion of lower vertebra L5 and the transverse process of upper vertebra L4 but not the spinous process for either vertebra FIG. 38 depicts a sagittal view of one embodiment in which conformable ligature 14 may be passed around the pedicle portion and through the posterior portion of spinous process SP on lower vertebra L5.

In some embodiments, the surgeon may pass conformable ligature 14 alternative ways due to disease, injury, tumor, degenerative effects or the like. For example, FIG. 33 depicts a posterior view of one embodiment in which conformable ligature 14 may be passed through a portion of the pedicle of lower vertebra L5, which may allow system 100 to apply direct tension on lower vertebra L5. As another example, FIG. 34 depicts a sagittal view of one embodiment in which conformable ligature 14 may be passed around bone graft 230 and spinous process SP on lower vertebra L5 such that the lower portion of bone graft 230 may be prevented from moving posterior to the spine but may move anterior to the spine FIG. 35 depicts a posterior view of one embodiment in which conformable ligature 14 may be passed around a portion of the pedicle portion of lower vertebra L5, which may allow system 100 to indirectly apply tension on lower vertebra L5. FIG. 36 depicts a sagittal view of one embodiment in which conformable ligature 14 may be passed around bone graft 230 and spinous process SP on lower vertebra L5 such that the lower portion of bone graft 230 may be prevented from moving posterior or anterior to the spine. FIG. 37 depicts a posterior view of one embodiment in which first and second conformable ligatures 110 may be passed around a portion of the pedicle portion of lower vertebra L5. Advantageously, the system 100 may be able to selectively apply tension to either side of the spine. Furthermore, system 100 may be able to control movement between vertebrae L4 and L5 similarly to the embodiments depicted in FIGS. 33 and 34, but without contacting the spinous process SP of lower vertebra L5. FIG. 38 depicts a sagittal view of one embodiment in which conformable ligature 14 may be passed around the pedicle portion and through the posterior portion of spinous process SP on lower vertebra L5. Advantageously, vertebrae L4 and L5 may be able to move relative to each other but bone graft 230 may be held in place.

An advantage to bone fixing system 100 is that the position of blocking body 120 may be based on disease, injury, tumor, degenerative effects or the like. For example, FIG. 33 depicts one embodiment in which a single blocking body 120 may be positioned off-center of the spine. As another example, FIG. 34 depicts one embodiment in which blocking body 120 may be positioned abutting a bone such as spinous process SP. FIG. 35 depicts one embodiment in which blocking body 120 may be positioned centered on the midline of the spine. FIG. 36 depicts one embodiment in which blocking body 120 may be positioned some distance away from spinous process SP. FIG. 37 depicts one embodiment in which two blocking bodies 120 may be positioned lateral to bone graft 230 FIG. 38 depicts one embodiment in which blocking body 120 may be positioned centered between spinous processes SP.

Two or more conformable ligatures 14 and/or two or more blocking bodies 120 may be used to hold a bone, bone graft, tendon, rod, shaft, or other structure in a body. FIG. 36 depicts a posterior view and FIG. 37 depicts a sagittal view of one embodiment of a bone fixing system having two blocking bodies 120 and 120' and two conformable ligatures 14 and 14'. In some embodiments, bone fixing system 100 may include a first conformable ligature 14 passed around a bone such as transverse process TP on lumbar vertebra L4 and transverse process TP on lumbar vertebra L5, and a second conformable ligature 14' passed around a bone such as transverse process TP on lumbar vertebra L4 and transverse process TP on lumbar vertebra L5. Bone fixing system 100 with a first blocking body 120 on a first side of the spine and a second blocking body 120' on the second side of the spine may be used to straighten a spine. For example, tensioning one conformable ligature 14 greater than conformable ligature 14' may bias vertebrae to help straighten a curved spine.

Figure 39:
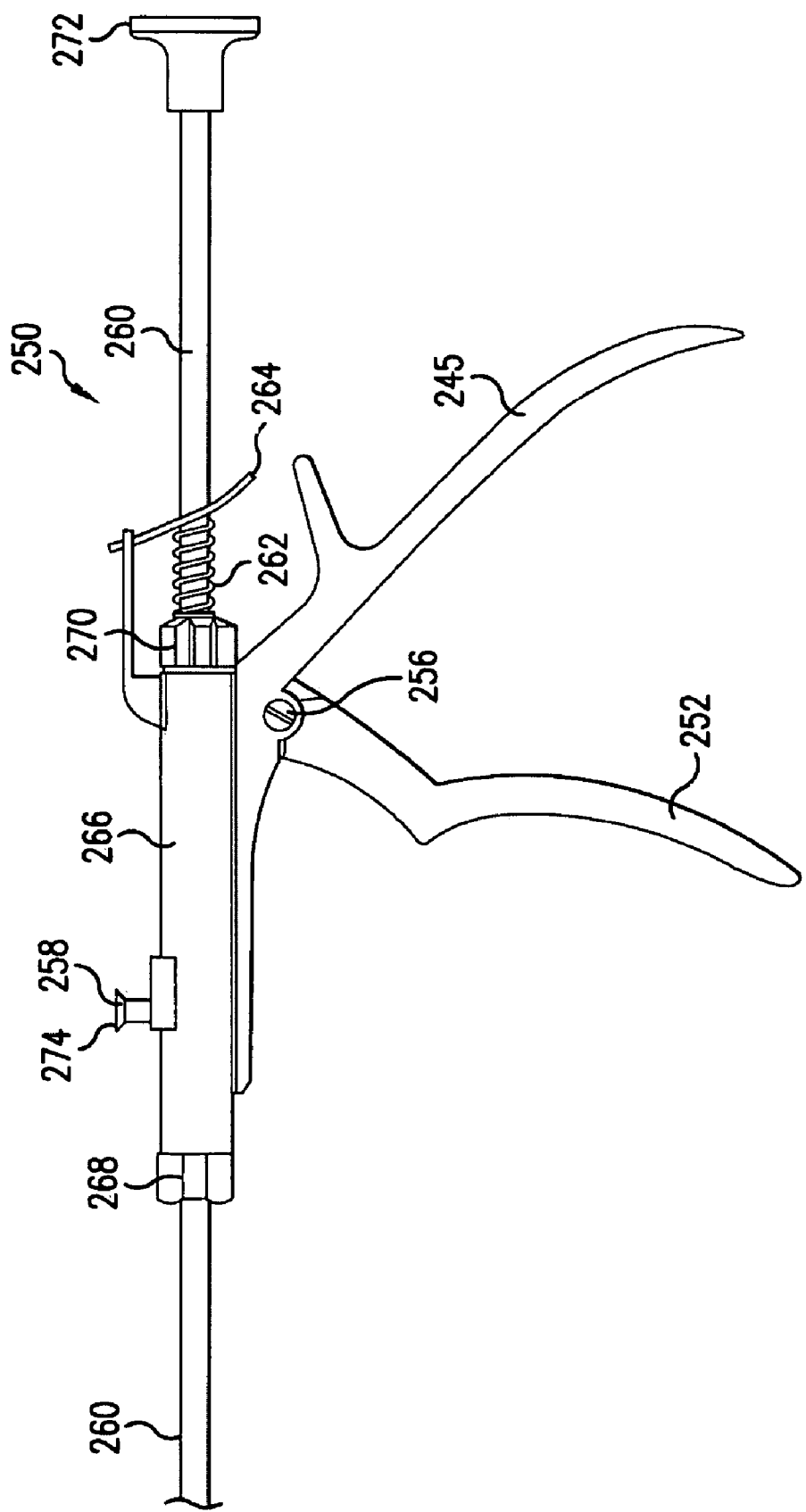
FIG. 39 depicts a side view of one embodiment of a tensioning tool for a bone fixing system.

FIG. 39 depicts a side view of a portion of one embodiment of tensioning tool 250, which may be used to apply tension to conformable ligature 14. As shown in FIG. 39, tensioning tool 250 includes tool body 266 for engaging conformable ligature 14, longitudinal member 260 for advancement in tool body 266, and distal end (such as distal end 154 depicted in FIGS. 14, 17, and 20) for engagement with blocking body 120. As shown in FIG. 39, tool body 266 includes attachment point 274 (with flange 258) for connection to ligature 14, fixed handle 254, movable handle 252 for rotation about axis 256, return spring 262, catch mechanism 264, return spring adjustment member 270, and spring adjustment member 268.

Attachment point 274 can attach first and second ends of conformable ligature 14 to tensioning tool 250. In some embodiments, attachment point 274 may include flange 258 for preventing first and second ends of conformable ligature 14 from detaching from tensioning tool 250. Distal end 154 (such as the embodiments shown in FIGS. 14, 17, and 20) of tensioning tool 250 may engage to a portion of blocking body 120. Fixed handle 254 may be gripped by a surgeon, movable handle 252 may be rotated about axis 256, such as by squeezing movable handle 252, to longitudinal member 260 through tool body 266 a selected distance. Advancing longitudinal member 260 to move blocking body 120 away from tool body 266 while maintaining first and second ends of conformable ligature 14 on attachment point 274 applies tension to conformable ligature 14. In some embodiments, the selected distance longitudinal member 260 advances through tool body 266 may be proportional to the tension applied to conformable member 110.

In some embodiments, tool body 266 may include return spring 262, catch mechanism 264, and return spring adjustment member 270 for controlling the distance that longitudinal member 260 is allowed to return when movable handle 252 is released. In some embodiments, return spring 262 may bias catch mechanism 264 such that movement is permitted in one direction only. In some embodiments, return spring 262 may bias catch mechanism 264 such that longitudinal member 260 may only move forward through tool body 266. Advantageously, return spring 262 may ensure that a surgeon does not inadvertently relieve tension from conformable ligature 14. In other words, tensioning tool 250 may have a default configuration for tensioning conformable ligature 14. In some embodiments, actuating catch mechanism 264 (such as a surgeon pressing on catch mechanism 264 with a thumb) may change the positioning of catch mechanism 264 such that movement of longitudinal member 260 is permitted in a reverse direction as well. In some embodiments, movement of longitudinal member 260 in a reverse direction may include changing the positioning of catch mechanism 264 in relation to longitudinal member 260 as well as pulling in a reverse direction on grasping member 272.

In some embodiments, tensioning tool 250 may include spring adjustment member 268 for adjusting the compression on a spring (not shown) in body 266. In some embodiments, rotating spring adjustment member 268 one direction, spring adjustment member 268 may be advanced some distance into body 266 such that a spring may be compressed. In some embodiments, rotating spring adjustment member 268 in the other direction, spring adjustment member 268 may be advanced some distance out of body 266 such that compression forces on the spring may be relieved. By changing the compression forces on the spring, the spring may exert more or less force on longitudinal member 260, which may affect how much tension can be applied to the ends of conformable ligature 14.

In some embodiments, ligature 14 may be passed around elongate members 210, bone fastener assemblies 212, vertebrae (such as L5), and other tendons, muscles, plates or other anatomical or implanted structures and the ends of ligature 14 may be passed into a portion of blocking body 120, such that a loop is formed extending from a first portion of blocking body 120. In some embodiments, first and second ends of ligature 14 may be passed through a passage in blocking body 120. In some embodiments, a passage may be formed by inner surface 125 of blocking body 120 and first surface 146 of compression member 140. In some embodiments, first and second ends of ligature 14 may exit by passing out of one or more exit passages 128 in blocking body 120.

Distal end 154 of tensioning tool 250 engages blocking body 120. In some embodiments, distal end 154 of longitudinal member 260 may conform to the shape or profile of blocking body 120. In some embodiments, distal end 154 of longitudinal member 260 may be configured with features for engaging one or more features on blocking body 120. In some embodiments, first and/or second ends of ligature 14 may be attached to tensioning tool 250. In some embodiments, first and/or second ends of ligature 14 may be attached to attachment point 274 located on tool body 266. In some embodiments, movable handle 252 of tensioning tool 250 may be rotated about axis 256 to advance longitudinal member 260 through tool body 266. The advancement of longitudinal member 260 through tensioning tool 250 moves attachment point 274 away from blocking body 120, pulling ends of ligature 14 to decrease the size of the loop, and further advancement tensions ligature 14. In some embodiments, the tension applied to ligature 14 may be sufficient to hold one or more structures in a desired position. In some embodiments, the tension applied to ligature 14 may be sufficient to hold a bone in a position. In some embodiments, the tension applied to ligature 14 may be sufficient to pull one or more bones or structures into alignment. For example, tensioning tool 250 may provide sufficient tension to one or more ends of ligatures 14 (depicted in FIG. 31) to pull vertebra L5 (depicted in FIG. 32) in alignment with the natural curvature of the spine.

In some embodiments, once an appropriate tension has been applied to ligature 14, closure member 130 may be actuated to create a friction force to restrict movement of ligature 14 relative to blocking body 120, or to impinge ligature 14 in blocking body 120. In some embodiments, closure member 130 may be pre-installed in blocking body 120. In some embodiments, closure member 130 may be inserted in blocking body 120 after engagement of blocking body 120 by tensioning tool 250. In some embodiments, closure member 130 may be inserted through distal end 154 of longitudinal member 260 into blocking body 120.

In some embodiments, once closure member 130 has engaged threads 122 in blocking body 120 to provide a desired friction force to impinge ligature 14 in blocking body 120, first and second ends of ligature 14 may be disconnected from tensioning tool 250. Once ligature 14 has been disconnected from tensioning tool 250, tensioning tool 250 may be disengaged from blocking body 120.

The tensioning tool of FIG. 39 can use a ratcheting motion to advance longitudinal member 260. Each time the surgeon squeezes handles 252 and 254 together, longitudinal member 260 advances a predefined distance, typically greater than 10 mm. While tensioning tool 250 works well in surgical procedures, it has several shortcomings. Because longitudinal member 260 advances the same amount with each pull of handle 252, the surgeon must tension ligature 14 in relatively large increments, but cannot tension ligature 14 to a position between the increments. In other words, tensioning tool 250 does not offer a full range of tensioning control as the attachment point can only be positioned at the increments determined by the ratcheting mechanism (e.g., every 10 mm or so). A corollary of this problem is that tension is applied in a pulsed manner to ligature 14 as the surgeon squeezes and releases the handles.

Another issue with tensioning tool 250 is that it is difficult for a surgeon to release a selected amount of tension in ligature 14. If a surgeon believes that ligature 14 has been over tensioned, the surgeon must typically release all or a large amount of tension in ligature 14 and begin tensioning ligature 14 again.

Moreover, tensioning tool 250 is relatively bulky. This makes it difficult to have multiple tensioning tools in place at the same time during a procedures. Consequently, tensioning multiple ligatures can be take a significant amount of time as the tensioning tool 250 may have to be removed from a surgical site each time a surgeon wishes to tension a new ligature. This especially inefficient in procedures in which a surgeon may wish to tension each ligature a little at a time rather than tensioning one ligature completely, then moving to the next ligature.

FIG. 40 is a diagrammatic representation of another embodiment of a tensioning tool 300 for tensioning a conformable ligature that overcomes the shortcomings of tensioning tool 250. Tensioning tool 300 comprises a tool body 305, a threaded drive shaft 310 and a movable carriage 315 engaged with the threads of drive shaft 310. The threads of drive shaft 310 can include any suitable thread shape including a symmetric v-thread, square thread, British acme thread, worm thread, buttress thread, metric acme thread or other suitable thread. Preferably, drive shaft 310 has a thread pitch of between 1-5 mm. Movable carriage 315 is engaged with the threads of drive shaft 310 and moves along slot 320 in tool body 305 when drive shaft 310 rotates. Slot 320 can partially overlap carriage 315 to capture carriage 315 in slot 320. In other embodiments, carriage 315 can be held in place by drive shaft 310. Carriage 315 carries tensioning member 325 that acts as an attachment point for a conformable ligature. Tensioning tool 300 further includes a handle that provides an ergonomic user control to rotate drive shaft 310. According to one embodiment, the handle can connect to drive shaft 310 using a quick connect 330. In other embodiments, the handle may be fixed. Preferably, all portions of tensioning tool are formed of biocompatible material such as stainless steel, titanium, a strong plastic or other material.

Tensioning tool 300 also includes a connector 335 shaped to interface with a ligature capturing implant (e.g., such as the connection parts shown in FIGS. 1-13 and blocking bodies shown in FIGS. 14-38). Connector 335 can be shaped to abut a variety of ligature capturing implants or connector 335 can be interchangeable such that a surgeon can select the appropriate interface member based on the type(s) of ligature capturing implants used in a particular procedure. According to one embodiment, connector 335 can simply abut the ligature capturing implant (including abutting a rod if the ligature capturing implant uses a rod) or, according to other embodiments, may attach to the ligature capturing implant. Connector 330 can include tangs 340 that define an open area 345 through which the ends of the conformable ligature can pass so that a portion of conformable ligature can be looped around tensioning member 325.

FIG. 41 is a diagrammatic representation of a cross section of one embodiment of tensioning tool 300 showing tool body 305, drive shaft 310, carriage 315, tensioning member 325, quick connect 330 and connector 335. While various components such as body 305 and drive shaft 310 are each shown as being single pieces, they may comprise multiple parts. For example, drive shaft 310 can include a threaded portion that connects to a non-threaded portion. As another example, tool body 305 may comprise multiple pieces.

As illustrated in FIG. 41, carriage 315 defines a threaded passage 355 that engages the threads of drive shaft 310. As drive shaft 310 rotates, carriage 315 will move either towards or away from connector 335 along slot 320 depending on the direction of rotation of drive shaft 310. In the embodiment of FIG. 41, rotation occurs about an axis that is substantially parallel to the primary direction of movement of tensioning member 325. The tension in a conformable ligature looped about or otherwise attached to tensioning member 325 will increase or decrease depending on the direction of rotation. Tensioning member 325 may include flange 360 for preventing the conformable ligature from detaching from tensioning tool 300.

Tensioning tool 300 further includes a handle that provides an ergonomic user control to rotate drive shaft 310. According to one embodiment, the handle can connect to drive shaft 310 at quick connect 330. At the other end, drive shaft 310 can rest in a drive shaft seat 364 that is movable in tool body 305. A spring 365 between drive shaft seat 364 and tool body 305 allows drive shaft 310 to be pushed towards connector 335. This can dampen forces applied to the drive shaft towards connector 335 (e.g., by the surgeon inadvertently pushing on then handle). Furthermore, since spring 365 will have a known displacement per unit force applied, a measure of displacement of spring 365 indicates how much tension is applied to the ligature (i.e., the force from the tensioned ligature is transferred through carriage 315 to drive shaft 310 to compress spring 365 a known displacement). According to one embodiment, tensioning tool 300 can include features (such as extensions 366) that are coupled to the drive shaft. Extensions 366 move forward as drive shaft 310 moves forward when spring 365 compresses. The position of extensions 366 can be compared to markings on body 305 to determine the force applied to the ligature. Preferably, spring 365 is selected so that spring 365 is fully compressed at between 500 Newtons and 1500 Newtons.

In operation, a surgeon can form a loop about one or more structures with a conformable ligature and a ligature capturing implant Examples of ligature capturing implants are shown in FIGS. 1-28, though any ligature capturing implant known or developed in the art can be used. Examples of a conformable ligature looped about one or more structures are shown in FIGS. 29-38. The structures can include bones, rods and other structures in a patient's body. Initially, the surgeon can configure the ligature capturing implant to allow tightening of the ligature. Another portion of the ligature can be coupled to tensioning tool 300 at tensioning member 325. According to one embodiment, the conformable ligature is attached by creating a loop with the free ends of the ligature (e.g., such as ends 42 and 44 of FIG. 6C). This can be done using pins, brackets, metal attachments, sewing, a knot, a clamp or other mechanism for forming the free ends into a loop. In other embodiments, the conformable ligature may be clamped to a portion of tool 300 or otherwise attached to tool 300.

Before or after attaching the ligature to tensioning member 325, the surgeon can bring connector 335 into contact with the ligature capturing body so that connector 335 pushes against the ligature capturing body as the ligature is tensioned. Rotating drive shaft 310 causes carriage 315 to move along slot 320. As carriage 315 moves, a portion of the conformable ligature is pulled causing the loop about the various structures to tighten. When the surgeon determines that the ligature is sufficiently tightened about the structures to be fixed, the surgeon can tighten the ligature capturing implant so that the ligature does not move within the ligature capturing implant thereby securing the loop about the structures. In other embodiments, the ligature capturing implant may be configured to allow the ligature to be tightened but not loosened. Consequently, once the surgeon is satisfied with the tension in the loop, the surgeon does not have to further adjust the ligature capturing implant to prevent loosening of the loop.

Preferably, tensioning tool 300 can apply a tensioning force of at least between 300 and 1500 Newtons to the conformable ligature.

When the loop about the structures is secure, the surgeon can rotate drive shaft 310 in the opposite direction to move carriage 315 towards connector 335. This will release the tension from the portion of the ligature between tensioning member 325 and the ligature capturing implant to allow the surgeon to remove the tensioning tool 300.

The embodiment of FIGS. 40 and 41 provides several advantages over the embodiment of FIG. 39. First, the movement speed and placement of carriage 315 can be finely controlled by controlling rotation of drive shaft 310. This allows the surgeon to have continuous control over the tensioning process and greater control over the final tension of the ligature when compared to the pulsed tensioning provided by the embodiment of FIG. 39. Furthermore, the surgeon can easily reduce the tension in the ligature by small, controllable amounts simply by rotating drive shaft 310 in the opposite direction. Consequently, if the surgeon deems that the ligature is too tight, the surgeon can rotate drive shaft 310 in the appropriate direction until the ligature is at the appropriate lower tension. This is a simpler process than having to release a relatively large amount of tension and then retention the ligature to the desired tension.

Another advantage is provided in procedures in which multiple ligatures are being installed. In some cases, surgeons find it desirable or necessary to use multiple ligatures. In such procedures, the surgeon will often want to tension each ligature a little at a time. For example, if there are three ligatures, the surgeon will tension the first ligature a small amount, then tension the second ligature a small amount, then tension the third ligature a small amount, then return to the first ligature and tension it some more and so on until all the ligatures are tensioned the appropriate amount. The embodiments of FIGS. 40 and 41 provide an advantage for this type of procedure because they are less bulky. This allows tensioning tool 300 to be left in place during a procedure so that the surgeon can tension other ligatures with other similar tensioning tools without removing tensioning tool 300. Consequently, multiple tensioning tools can be during a procedure to progressively tension a number of ligatures. Thus, efforts can be divided along the spine during a reduction procedure so that reduction is continuous.

Figure 42A:
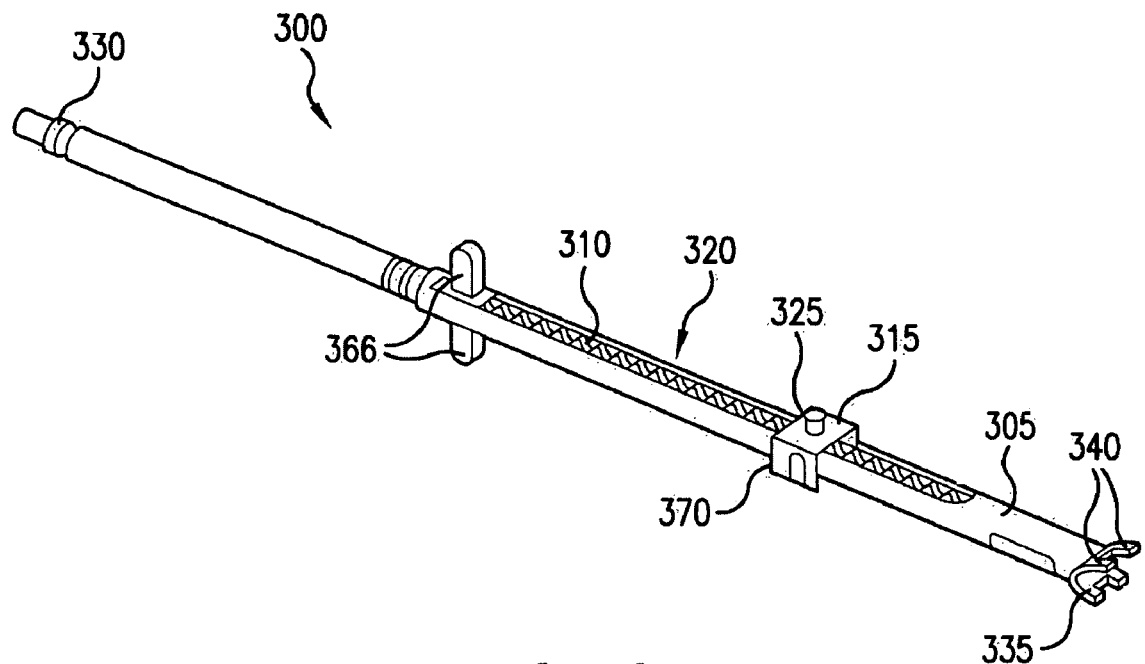
FIGS. 42A-42B are diagrammatic representations of another embodiment of a tensioning tool.
Figure 42B:
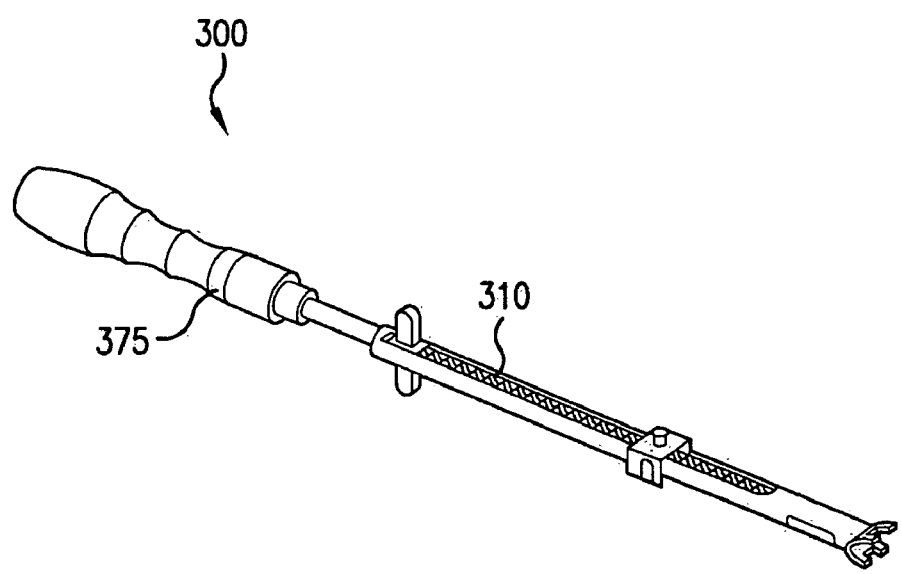

FIGS. 42A and 42B illustrate another embodiment of a tensioning tool 300. Tensioning tool 300 comprises a tool body 305 and a threaded drive shaft 310. A movable carriage 315 is engaged with the threads of drive shaft 310 and moves along slot 320 in tool body 305. Slot 320 can partially overlap carriage 315 to capture carriage 315 in slot 320. In other embodiments, carriage 315 can be held in place by drive shaft 310. Carriage 315 carries tensioning member 325 that acts as an attachment point for a conformable ligature. Tensioning tool 300 further includes a handle that provides an ergonomic user control to rotate drive shaft 310. According to one embodiment, the handle can connect to drive shaft 310 using a quick connect 330.

Tensioning tool 300 also includes a connector 335 shaped to interface with a ligature capturing implant (e.g., such as the connection parts shown in FIGS. 1-13 and blocking bodies shown in FIGS. 14-38). Connector 335 can be shaped to abut a variety of ligature capturing implants or connector 335 can be interchangeable such that a surgeon can select the appropriate interface member based on the type(s) of ligature capturing implants used in a particular procedure. According to one embodiment, connector 335 can simply abut the ligature capturing implant or, according to other embodiments, may attach to the ligature capturing implant. Connector 330 can include tangs 340 that define an open area 345 through which the ends of the conformable ligature can pass so that a portion of conformable ligature can be looped around tensioning member 325.

FIGS. 42A and 42B further show extensions 366 that can move in slot 420 as drive shaft 310 moves (e.g., due to compression of spring 365 shown in the embodiment of FIG. 40). The position of extensions 366 can be used to determine the amount of force applied to the spring and hence the ligature.

In the embodiment of FIG. 42A, carriage 315 includes a portion 370 that is exterior to tool body 305. This portion can allow a surgeon to more easily grasp carriage 315 with fingers or a tool to allow the surgeon to manipulate carriage 315. This can be advantageous in embodiments such as shown in FIGS. 43A and 43B in which the orientation of the carriage can be changed to engage or disengage carriage 315 from drive shaft 310.

FIG. 42B is a diagrammatic representation of tensioning tool 300 with handle 375 attached Handle 375 provides an ergonomic interface for a surgeon to rotate drive shaft 310 and may be detachable or fixed. If the handle is detachable, a kit for tensioning tool 300 can include a variety of handles to allow a surgeon to select a preferred handle 375. In other embodiments, a motor may attach to drive shaft 310 to allow for motorized rotation of drive shaft 310.

Figure 43A:
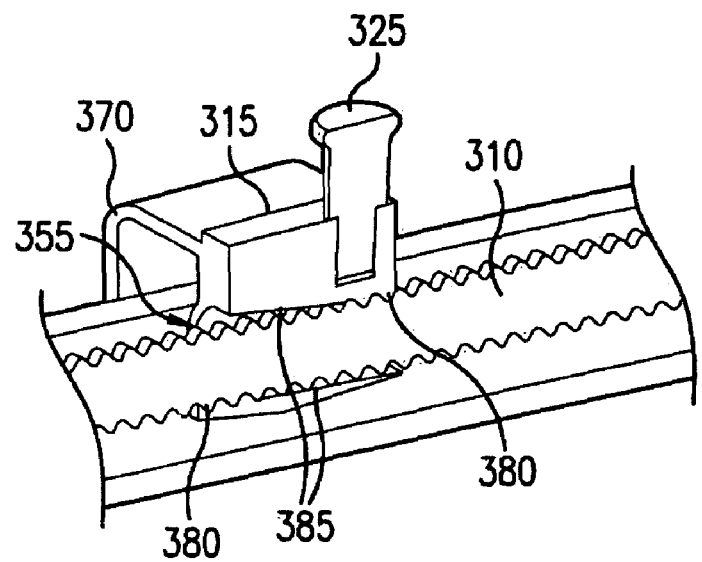
FIGS. 43A-43B are diagrammatic representations of a portion of a tensioning tool.
Figure 43B:
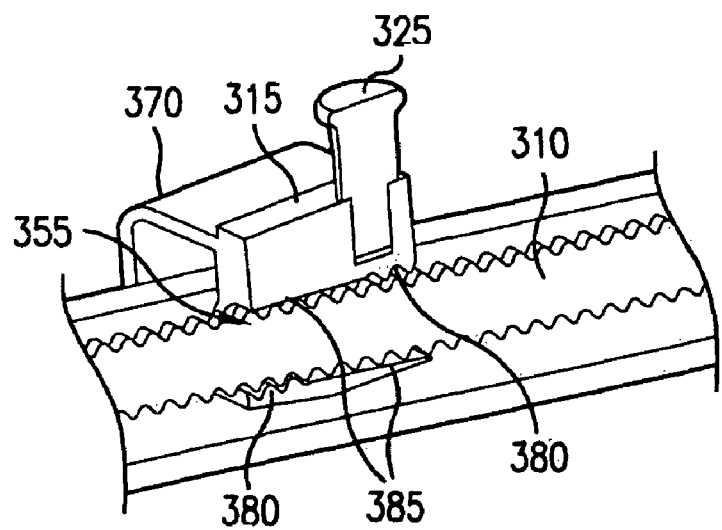

FIGS. 43A and 43B are diagrammatic representations of a view of carriage 315 carrying tensioning member 325 in a first orientation (FIG. 43A) and a second orientation (FIG. 43B) relative to drive shaft 310. Carriage 315 includes a drive shaft passage 355 through which drive shaft 310. Drive shaft passage can completely or partially encircle drive shaft 310. In the embodiments of FIGS. 43A and 43B, drive shaft passage 355 includes thread engaging portions 380 and unthreaded portions 385. Drive shaft passage 355 can be shaped and sized such that carriage 315 can rock slightly to selectively engage or disengaged thread engaging portions 380 with threads on drive shaft 310. According to one embodiment, the center of mass of carriage 315 can be positioned so that carriage 325 naturally rests in the orientation of FIG. 43A with thread engaging portions 380. In any case, when force is applied to tensioning member 325 by a tensioned ligature, carriage 315 will tend to rotate to engage thread engaging portions 380. Carriage 315 can be rotated slightly to disengage thread engaging portions 380. This can allow a user to easily slide carriage 315 to a desired position. For example, a user can apply force by hand or with a tool to portion 370 to rotate carriage 315 from the position shown in FIG. 43A to the position shown in FIG. 43B to slide carriage 315 in either direction along drive shaft 310.

The ability to selectively disengage thread engaging portions 380 so that the user can slide carriage 315 may make the various portions of the tensioning procedure more efficient. Rather than having to rotate drive shaft 310 to move carriage 315 to a position in which the conformable ligature begins to tension, a user can slide carriage 315 to that position (or other desired position) and then rotate drive shaft 310 to further tension the conformable ligature. Additionally, once the tension of the loop about the various structures in the body has been set by fully closing the ligature capturing implant to prevent loosening of the loop, the user can simply slide carriage 315 along drive shaft 310 to remove tension from the portion of the conformable ligature attached to tensioning member 325. Additionally, if for some reason a user determines that tension must be released from the conformable ligature quickly, the user can do so by sliding carriage 315 rather than rotating drive shaft 310.

In the embodiment of FIGS. 43A and 43B, drive shaft passage 355 includes thread engaging portions 380 on the top portion of one end and the bottom portion of the other end. In other embodiments, drive shaft passage 355 may include a thread engaging portion 380 at just one end or at any suitable point along drive shaft passage 355.

Figure 44:
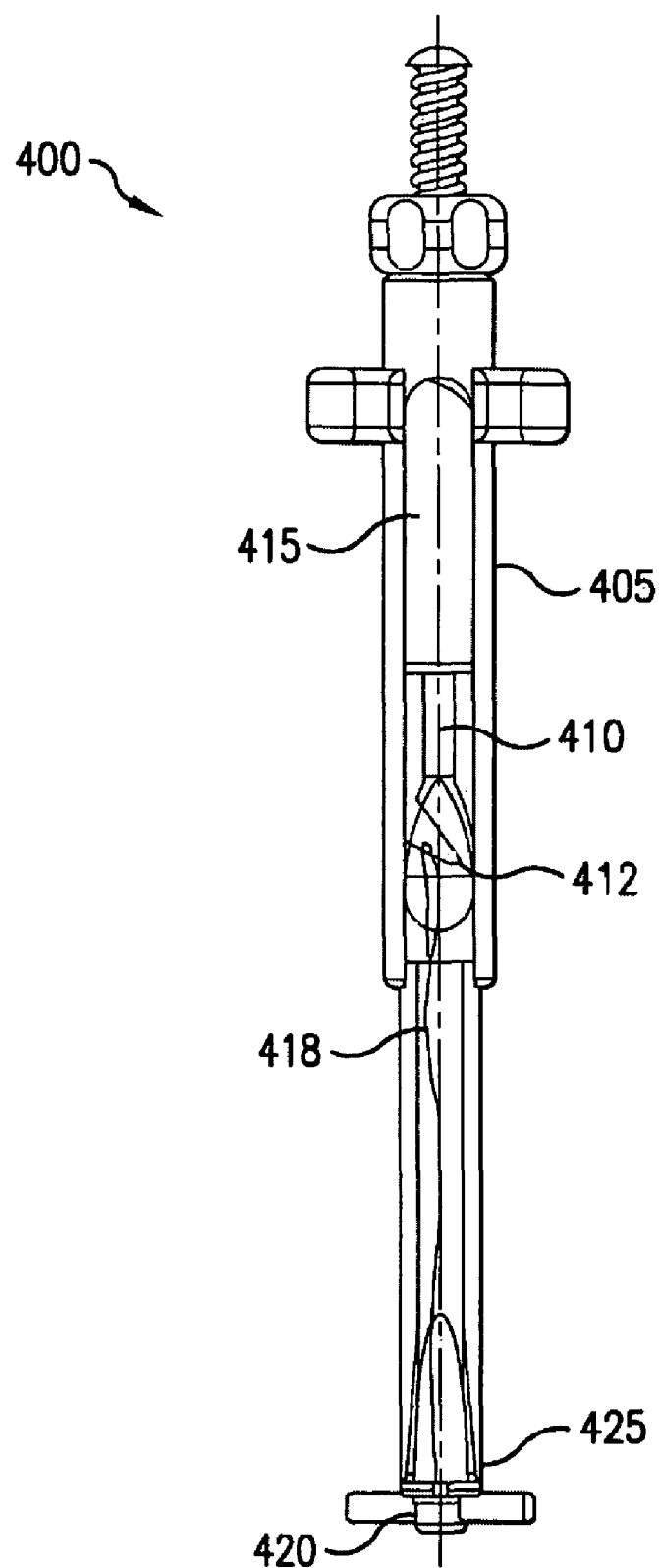
FIG. 44 is a diagrammatic representation of yet another embodiment of a tensioning tool.

In the previous embodiments, tensioning member 325 is carried by carriage 315 that moves along drive shaft 310 as drive shaft 310 rotates. In other embodiments, the tensioning member is located at the end of a movable shaft. FIG. 44 is a diagrammatic representation of another embodiment of a tensioning tool. In the embodiment of FIG. 44, a tensioning tool 400 can include a tool body 405, a tensioning member shaft 410 and a rotatable column 415. Tensioning member shaft 410 carries a tensioning member 412 in the form of a hook. Tensioning member shaft 410 can include threads that engage with rotatable column 415. Rotation of column 415 can cause shaft 410 to actuate to move tensioning member 412 towards or away from ligature capturing implant 420. In the embodiment of FIG. 44, a user can loop a portion of the conformable ligature 418 about tensioning member 425 and rotate column 415 to actuate shaft 410 to increase or release tension in the conformable ligature.

Tensioning tool 400 can include an end 425 that contacts ligature capturing implant 420. According to one embodiment, the end of tensioning tool 400 can act as a tool portion to tighten a rotatable ring or other portion of ligature capturing implant 420 to capture the conformable ligature in ligature capturing implant 420. As one example, end 425 can be adapted to engage with tool portions 134 of the ligature capturing implant shown in FIG. 25.

Thus, like the embodiments of FIGS. 40-42B, the embodiment of FIG. 44 includes a first portion in threaded engagement with a second portion. Rotation of the portions relative to each other causes translation of tensioning member 412. The position of tensioning member 412 can be continuously controlled, avoiding the shortcomings of pulsed tensioning. Additionally, the tension can be easily released by rotating the portions of tensioning tool 400 in an opposite direction to move tensioning member 412 closer to ligature capturing implant 420.

In the above embodiments, a portion of the tensioning tool is rotated to translate a tensioning member. While specific embodiments are shown, other embodiments of translating a tensioning member can be used. For example, the tensioning member can be coupled to the tool body. As a shaft advances due to rotation either of the shaft or another portion of the tensioning tool in threaded engagement with the shaft, the tool body and consequently, the tensioning member can be pushed away from the ligature capturing implant causing tension in the ligature to increase. The tension can be reduced by rotating the portions of the tensioning tool in threaded engagement in the opposite direction relative to each other.

According to various embodiments, a surgical procedure can be performed using a tensioning tool that provides continuous control over tensioning the ligature. A user can form a loop about one or more structures in a patient's body with a conformable ligature and a ligature capturing implant. The ligature capturing implant can include ligature capturing comprising rods, compression members or other ligature capturing implant. The structures can include, for example, a bone, a bone fastener, a tendon, a bone graft, a plate, a rod or other structure in the body. For example, the loop can be placed about a portion of a vertebra. The user can attach a portion of the conformable ligature to a tensioning member of a tensioning tool that provides a continuous range of control. The tensioning tool can comprise a first portion in threaded engagement with a second portion. The user can rotate the first portion relative to the second portion to move the tensioning member to tension the loop. For example, a user can rotate a drive shaft to move a carriage carrying the tensioning member. In some embodiments, the user can disengage the carriage from the drive shaft and slide the carriage along the drive shaft to a selected position. As another example, the user can rotate a portion of a tool engaged with a threaded shaft to cause the cause the shaft to move. The first portion can also be rotated relative to the second portion in an opposite direction to release tension from the loop. The method can further comprise positioning the tensioning tool so that a connecting portion of the tensioning tool abuts the ligature capturing implant.

According to one embodiment, a spinal reduction can be performed using tensioning tools. A method of progressive spinal reduction can comprise forming multiple loops about structures in a patient's body with multiple conformable ligatures and ligature capturing implants and partially tensioning each conformable ligature in turn with a corresponding tensioning tool until each conformable ligature is at a desired tension to perform spinal reduction procedure. Tensioning each conformable ligature may comprise attaching a portion of that conformable ligature to a tensioning member of the corresponding tensioning tool, the corresponding tensioning tool comprising a first portion in threaded engagement with a second portion and rotating the first portion relative to the second portion to move the tensioning member away from a corresponding ligature capturing implant to tension that conformable ligature about at least a portion of a vertebra. The first portion is rotated relative to the second portion about an axis that is substantially parallel to a primary direction of movement of the tensioning member.

Another embodiment of a method comprises providing a tensioning tool comprising, a tool body defining a slot, a threaded drive shaft running through at least a portion of the tool body, a tensioning member and a carriage coupled to the tensioning member. The carriage defines a drive shaft passage having at least one thread engaging portion to engage threads on the drive shaft. The drive shaft passes through the drive shaft passage. The method further comprises forming a loop about one or more structures in a patient's body with a conformable ligature and a ligature capturing implant, coupling a portion of the conformable ligature to the tensioning member and rotating the drive shaft to move the carriage away from the ligature capturing implant to tension the conformable ligature. Embodiments can also include rotating the drive shaft the opposite direction to release tension from the loop. The structures about which the loop is formed can include, for example, a bone, a bone fastener, a tendon, a bone graft, a plate, a rod or other structure in the body. For example, the loop can be located about at least a portion of a vertebra for a spinal reduction procedure.

According to one embodiment, the drive shaft passage of the carriage includes one or more additional unthreaded portions. The method can further comprise rotating the carriage to disengage the at least one thread engaging portion from the threaded drive shaft and sliding the carriage along the drive shaft to a desired position.

Another embodiment of a method comprises passing a conformable ligature around one or more structures in a body, passing first and second ends of the conformable ligature through a loop passage in a ligature capturing implant to form a loop, adjusting the ligature capturing implant to increase to resistance on the movement of the conformable ligature to a selected amount that allows the conformable ligature to move through the ligature capturing implant when a force is applied to the conformable ligature, attaching a portion of the conformable ligature to a tensioning member of a tensioning tool, rotating a threaded drive shaft of the tensioning tool to move the tensioning member to apply tension to the conformable ligature and adjusting the ligature tensioning implant to prevent the loop from loosening. According to one embodiment, rotating a threaded drive shaft of the tensioning tool to move the tensioning member comprises rotating the threaded drive shaft to move a carriage coupled to the tensioning member. The carriage can define a drive shaft passage having at least one thread engaging portion to engage threads on the drive shaft and wherein the drive shaft passes through the drive shaft passage. The method can further comprise positioning the tensioning tool so that a connecting portion of the tensioning tool abuts the ligature capturing implant. According to one embodiment the drive shaft can be rotated in an opposite direction to release tension from the conformable ligature.

According to one embodiment a drive shaft passage can include one or more additional unthreaded portions. The method can further include rotating the carriage to disengage the at least one thread engaging portion from the threaded drive shaft and sliding the carriage along the drive shaft to a desired position.

Another embodiment comprises a tensioning tool providing continuous control of conformable ligature tension, comprising a tool body defining a slot, a connection portion shaped to at least abut a ligature capturing implant, a threaded drive shaft running through at least a portion of the tool body, a tensioning member and a carriage coupled to the tensioning member, the carriage defining a drive shaft passage having at least one thread engaging portion to engage threads on the drive shaft and wherein the drive shaft passes through the drive shaft passage, wherein rotation of the drive shaft causes the carriage to move towards or away from the connection portion. According to one embodiment, the carriage is configured to be rotated from a first position in which the at least one thread engaging portions are engaged with threads on the drive shaft to a second, slidable position, in which the at least one thread engaging portions are not engaged with the threads of the drive shaft. The tensioning tool can further comprise a drive shaft seat in which a first end of the drive shaft is seated, a spring that compresses between the drive shaft seat of and the tool body, and a removable handle connected to a second end of the drive shaft distal from the first end.

The foregoing specification and accompanying figures are for the purpose of teaching those skilled in the art the manner of carrying out the disclosure and should be regarded in an illustrative rather than a restrictive sense. As one skilled in the art can appreciate, embodiments disclosed herein can be modified or otherwise implemented in many ways without departing from the spirit and scope of the disclosure and all such modifications and implementations are intended to be included within the scope of the disclosure as set forth in the claims below.

What is claimed is:

1. A method of progressive spinal reduction comprising:
    forming multiple loops about structures in a patient's body with multiple conformable ligatures and ligature capturing implants; and
    partially tensioning each conformable ligature in turn with a corresponding tensioning tool until each conformable ligature is at a desired tension to perform spinal reduction procedure, wherein tensioning each conformable ligature comprises:
    attaching a portion of that conformable ligature to a tensioning member of the corresponding tensioning tool, the corresponding tensioning tool comprising a first portion in threaded engagement with a second portion; and
    rotating the first portion relative to the second portion to move the tensioning member away from a corresponding ligature capturing implant to tension that conformable ligature about at least a portion of a vertebra, pulling the vertebra in alignment with a natural curvature of the spine, wherein the first portion is rotated relative to the second portion about an axis that is substantially parallel to a primary direction of movement of the tensioning member and that is substantially orthogonal to a plane relative to the spine.

2. The method of claim 1, wherein rotating the first portion relative the second portion to move the tensioning member comprises rotating a drive shaft to move a carriage carrying the tensioning member.

3. The method of claim 2, further comprising: disengaging the carriage from the drive shaft; sliding the carriage along the drive shaft to a selected position.

4. The method of claim 1, further comprising rotating the first portion relative to the second portion in an opposite direction to release tension.

5. The method of claim 1, further comprising leaving each tensioning tool in place while others of the multiple conformable ligatures are being tensioned.

6. A method of fixing structures in a patient's body comprising:
    providing a tensioning tool comprising:
        a tool body defining a slot;
        a threaded drive shaft running through at least a portion of the tool body;
        a carriage movable along the slot, the carriage defining a drive shaft passage having at least one thread engaging portion to engage threads on the drive shaft and wherein the drive shaft passes through the drive shaft passage;
        a connecting portion located at a distal end of the tensioning tool and shaped to interface with a ligature capturing implant; and
        a tensioning member coupled to the carriage;
    forming a loop about multiple structures in a patient's body with a conformable ligature and the ligature capturing implant;
    interfacing the tensioning tool and the ligature capturing implant via the connecting portion;
    coupling a portion of the conformable ligature to the tensioning member of the tensioning tool; and
    rotating the drive shaft to move the carriage and the tensioning member away from the ligature capturing implant to tension the conformable ligature; wherein forming the loop comprises forming the loop about at least a portion of a vertebra and pulling the vertebra in alignment with a natural curvature of the spine in a progressive reduction procedure.

7. The method of claim 6, wherein the drive shaft passage includes one or more additional unthreaded portions.

8. The method of claim 7, further comprising:
    rotating the carriage to disengage the at least one thread engaging portion from the threaded drive shaft; and
    sliding the carriage along the drive shaft to a desired position.

9. The method of claim 6, further comprising positioning the tensioning tool so that the connecting portion of the tensioning tool abuts the ligature capturing implant.

10. The method of claim 6, further comprising rotating the drive shaft the opposite direction to release tension from the loop.

11. The method of claim 6, further comprising tensioning one or more additional conformable ligatures that are looped about the multiple structures using one or more additional tensioning tools.

12. A method for holding a bone in a position, the method comprising:
    passing a conformable ligature around multiple structures in a body;
    passing first and second ends of the conformable ligature through a loop passage in a ligature capturing implant to form a loop;
    adjusting the ligature capturing implant to increase a resistance on the movement of the conformable ligature to a selected amount that allows the conformable ligature to move through the ligature capturing implant when a force is applied to the conformable ligature;
    interfacing the ligature capturing implant with a connecting portion of a tensioning tool;
    attaching a portion of the conformable ligature to a tensioning member of the tensioning tool; and
    rotating a threaded drive shaft of the tensioning tool about an axis of rotation to move the tensioning member in a primary direction of movement to apply tension to the conformable ligature, wherein the axis of rotation is substantially parallel to the primary direction of movement of the tensioning member; wherein forming the loop comprises forming the loop about at least a portion of a vertebra and pulling the vertebra in alignment with a natural curvature of the spine in a spinal reduction procedure.

13. The method of claim 12, wherein rotating a threaded drive shaft of the tensioning tool to move the tensioning member comprises rotating the threaded drive shaft to move a carriage coupled to the tensioning member, wherein the carriage defines a drive shaft passage having at least one thread engaging portion to engage threads on the drive shaft and wherein the drive shaft passes through the drive shaft passage.

14. The method of claim 13, wherein the drive shaft passage includes one or more additional unthreaded portions.

15. The method of claim 14, further comprising:
    rotating the carriage to disengage the at least one thread engaging portion from the threaded drive shaft;
    sliding the carriage along the drive shaft to a desired position.

16. The method of claim 15, further comprising positioning the tensioning tool so that the connecting portion of the tensioning tool abuts the ligature capturing implant.

17. The method of claim 15, further comprising rotating the drive shaft the opposite direction to release tension from the conformable ligature.

18. The method of claim 13, further comprising tensioning one or more additional conformable ligatures that are looped about the multiple structures using one or more additional tensioning tools.

* * * * *